United States Patent [19]

Roszkowski et al.

[11] 4,088,771
[45] May 9, 1978

[54] 1-LOWER ALKYL-4,5-DIHYDRO-5-PHENYL-2-LOWER ALKOXY CARBONYLAMINOIMIDAZOLES AND SUBSTITUTED PHENYL DERIVATIVES THEREOF

[75] Inventors: Adolph P. Roszkowski, Saratoga; Colin C. Beard; Charles Dvorak, both of Palo Alto; Klaus Weinhardt, Redwood City, all of Calif.

[73] Assignee: Syntex (U.S.A.) Inc., Palo Alto, Calif.

[21] Appl. No.: 708,651

[22] Filed: Jul. 26, 1976

[51] Int. Cl.² .............. A61K 31/415; C07D/233/48
[52] U.S. Cl. ......................... 424/273 R; 548/315 C07D/233/48
[58] Field of Search .................. 260/309.6, 309.7; 424/273; 548/315

[56] References Cited

PUBLICATIONS

Atkins et al., J. Chem. Soc. (London), Perkin Trans. I., 1973 (22), pp. 2644–2646.

Matier et al., J. Med. Chem. 1973, vol. 16, pp. 901–908.
Mengelberg, Chem. Abst., 1959, vol. 53, cols. 2210–2211.

Primary Examiner—Natalie Trousof
Attorney, Agent, or Firm—Tom M. Moran

[57] ABSTRACT

1-Lower alkyl-4,5-dihydro-5-phenyl-2-lower alkoxycarbonylaminoimidazoles, and substituted phenyl derivatives thereof, and pharmaceutically acceptable salts thereof, and methods of preparing such compounds. In one method, the compounds can be prepared by treating the corresponding β-lower alkylamino-β-(phenyl or substituted phenyl)-ethylamine with the desired 1,3-bis (alkoxycarbonyl)-S-methylisothiourea or 1-alkoxycarbonyl-S-methylisothiourea. The compounds can also be prepared by treating the corresponding 1-lower alkyl-2-amino-4,5-dihydro-5-(phenyl or substituted phenyl)-imidazole with the desired dialkylcarbonate. The subject compounds are useful as psychotherapeutic agents in treating or palliating abnormal conditions, in mammals, which involve the central nervous system.

57 Claims, No Drawings

1-LOWER ALKYL-4,5-DIHYDRO-5-PHENYL-2-LOWER ALKOXY CARBONYLAMINOIMIDAZOLES AND SUBSTITUTED PHENYL DERIVATIVES THEREOF

BACKGROUND OF THE INVENTION

1. The Invention

This invention relates to 1-lower alkyl-4,5-dihydro-5-(phenyl and substituted phenyl)-2-alkoxycarbonylaminoimidazoles and pharmaceutically acceptable salts thereof and to methods of preparing such compounds. In a further aspect, this invention relates to 1-lower alkyl-4,5-dihydro-5-(phenyl and monosubstituted phenyl)-2-alkoxycarbonylaminoimidazoles, and pharmaceutically acceptable salts thereof, and methods of preparing such compounds. In a still further aspect, this invention relates to 1-lower alkyl-4,5-dihydro-5-(disubstituted phenyl)-2-alkoxycarbonylaminoimidazoles, and pharmaceutically acceptable salts thereof, and methods of preparing such compounds. In another aspect, this invention relates to 1-lower alkyl-4,5-dihydro-5-(methylenedioxyphenyl)-2-alkoxycarbonylaminoimidazoles, and pharmaceutically acceptable salts thereof, and methods of preparing such compounds.

This invention also relates to methods of treating or palliating abnormal conditions involving the central nervous system, in mammals, e.g., depression, anxiety, convulsions, centrally-induced skeletal muscle spasm and spasticity by the administration of the compounds of the invention.

2. The Prior Art

A general discussion of psychotic disorders and the use of psychotropic drugs can be found in *The Pharmacological Basis of Therapeutics*, 4th Edition, L. S. Goodman and A. Gilman eds., McMillan Co., New York (1970).

In 1973 a group of 2-amino-4-aryl-2-imidazolines were described in the *Journal of Medicinal Chemistry*, Vol. 16, No. 8, page 901 (1973), primarily as anti-hypertensive agents but were also tested for a number of other biological activities including whether the compounds reversed or prevented the effect of reserpine on mice. This publication indicated that some 2-amino-4-aryl-2-imidazolines prevented the effect of reserpine-induced ptosis, induced by the administration of 2 mg/kg of reserpine, whereas others were inactive in this test. In contrast to the compounds described in the *Journal of Medicinal Chemistry*, the compounds of the present invention are N-alkyl 2-alkoxycarbonylamino-4-aryl-2-imidazolines, a number of which have been found to exhibit the ability to reverse hypothermia and ptosis induced by 5 mg/kg reserpine in laboratory animals; two well accepted assay methods for identifying compounds of clinical utility in the treatment of endogenous depression. In addition, a number of compounds of the present invention display mild tranquilizing and/or sedating properties in behavioral assays, and/or they have the ability to protect animals against various kinds of experimentally induced, convulsive seizure states and further exhibit centrally acting skeletal muscle relaxant properties. This spectrum of activities indicates that the compounds of the present invention possess a unique activity profile unlike that of any currently known psychotropic agents.

SUMMARY

In summary the compounds of the invention can be represented by the following generic formula:

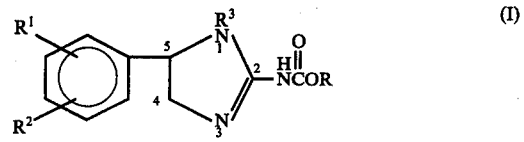

wherein

R and $R^3$ are each independently lower alkyl and the total number of carbon atoms in R and $R^3$ together is an integer of two through seven and (A) $R^1$ is hydrogen and $R^2$ is hydrogen, fluoro, chloro, bromo, iodo, alkyl of one through six carbon atoms, hydroxy, alkoxy of one through six carbon atoms, and trifluoromethyl; or (B) $R^1$ is at the 2-position on the phenyl ring and is chosen from the group of fluoro, chloro, bromo, iodo, hydroxy, alkoxy of one through six carbon atoms, alkyl of one through six carbon atoms, and trifluoromethyl and $R^2$ is the same as $R^1$ but is at the 3- or 5- position on the phenyl ring; or (C) $R^1$ is fluoro, chloro, bromo, iodo, hydroxy, methoxy, ethoxy, or methyl at any position on the phenyl ring and $R^2$ is the same as $R^1$ and is at any other position on the phenyl ring; or (D) $R^1$ and $R^2$ taken together may be methylenedioxy at adjacent positions on the phenyl ring.

Pharmaceutically acceptable salts of the above compounds are also encompassed within the scope of the invention.

A process of the invention comprises reacting a β-lower alkylamino-β-(substituted or unsubstituted phenyl)-ethylamine, or salt thereof, having the desired phenyl substituent with any of (a) 1-lower alkoxycarbonyl or 1,3-bis(lower alkoxycarbonyl)-S-methylisothiourea having the desired alkoxy substituent,

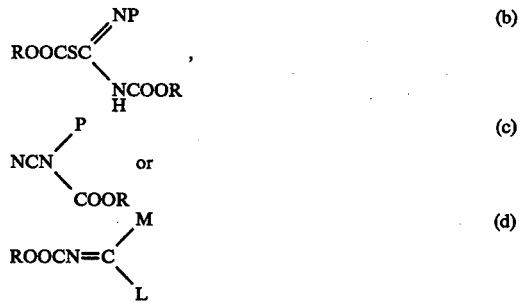

wherein P is hydrogen or COOR, R is lower alkyl, and M and L independently are chloro, lower alkoxy or lower alkylthio to yield the corresponding compound of formula (I).

An alternative process of the invention comprises reacting a 1-lower alkyl-2-amino-4,5-dihydro-5-(substituted or unsubstituted phenyl)-imidazole, or salt thereof, having the desired phenyl substituent, with a lower dialkylcarbonate, or alkyl chloroformate, having the desired alkyl substituent corresponding to R in the compounds of formula (I), to yield the corresponding compound of formula (I).

Further processes of the invention comprise methods of palliating or inhibiting psychic disorders and/or centrally induced musculoskeletal disorders, and/or convulsive disorders, in mammals, by the administration of an effective amount of the compounds of the invention.

The invention is further described hereinbelow.

FURTHER DESCRIPTION OF THE INVENTION AND PREFERRED EMBODIMENTS

Compounds of the Invention

The compounds of the invention can be represented by the following sub-generic formulas:

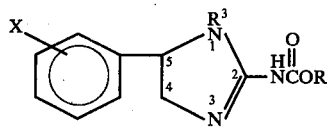

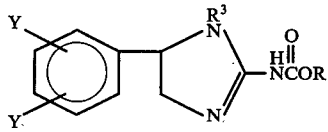

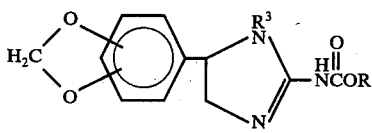

wherein

R and $R^3$ are independently lower alkyl with the total number of carbon atoms in R and $R^3$ taken together is from 2 to 7, inclusive;

X and Y are defined hereafter; and the methylenedioxy group of formula IV can be attached to any two adjacent carbon atoms on the phenyl ring.

In the compounds represented by formula (II), X is hydrogen, hydroxy, halo, trifluoromethyl, lower alkyl or lower alkoxy and is at any position on the phenyl ring. Preferably X is hydrogen, hydroxy, fluoro or chloro. Another preferred subgroup includes the compounds wherein the total number of carbons in R and $R^3$ is 2 or 3, i.e. both R and $R^3$ may be methyl or one ethyl and the other methyl, and X is hydrogen, halo, hydroxy, alkoxy of 1 through 3 carbons, trifluoromethyl or alkyl of 1 through 3 carbons. Typical illustrations of the preparation of the compounds of formula II can be had by reference to Examples 1-3 and 9-19.

Typical illustrations of the compounds for formula (III) can be had by reference to Examples 5-18. The compounds represented by formula (III) include, (A) those wherein each Y is hydroxy, fluoro, chloro, bromo, iodo, trifluoromethyl, the same lower alkoxy, or the same lower alkyl groups; the Y substituents are at the 2,3- or 2,5- positions and the total number of carbons in R and $R^3$ together is an integer of 2 through 7, and (B) those wherein each Y is fluoro, chloro, bromo, iodo, hydroxy, methoxy, ethoxy or methyl at any positions on the phenyl ring and the total number of carbons in R and $R^3$ together is 2 through 7.

Preferred compounds of group B include (i) those wherein the total number of carbons in R and $R^3$ together is 2 or 3; (ii) those wherein each Y is fluoro, hydroxy or methoxy; the total number of carbon atoms in R and $R^3$ together is an integer of 2 through 7; (iii) those wherein each Y is chloro or bromo with at least one Y being at the ortho position and the total number of carbon atoms in R and $R^3$ together is an integer of 2 through 5; (iv) those wherein each Y is iodo at an ortho position and the total number of carbon atoms in R and $R^3$ together is an integer of 2 through 5; (v) those wherein each Y is chloro at the 3,4- or 3,5- positions and the total number of carbons in R and $R^3$ together is 2 or 3; (vi) those wherein each Y is ethoxy with at least one Y at the ortho position on the phenyl ring and the total number of carbons in R and $R^3$ together is an integer of 2 through 5; (vii) those wherein each Y is methyl and may be at any position on the phenyl ring and the total number of carbons in R and $R^3$ together is 2 or 3; (viii) those wherein each Y is a methyl at a meta position on the phenyl ring and the total number of carbons in R and $R^3$ together is 4; and (ix) those wherein each Y is an ethoxy at an ortho position on the phenyl ring and the total number of carbons in R and $R^3$ together is 6.

Typical illustrations of the compounds of formula IV can be had by reference to Examples 4 and 9–12. Preferably the total number of carbon atoms in R and $R^3$ taken together is 2 or 3.

The compounds of the invention have an asymmetric carbon atom at the imidazole ring carbon atom to which the phenyl group is attached, namely the carbon at the 5 position, and thus exist as optically active isomers. Correspondingly, the above formulas are intended to represent the respective individual (+) and (−) optical isomers as well as mixtures thereof and accordingly the individual isomers as well as mixtures of the isomers (e.g. racemic mixtures) are encompassed within the invention. The compounds of the invention will be named herein, for purposes of convenience, as 1-alkyl-4,5-dihydro-5-(substituted phenyl)-2-alkoxycarbonylaminoimidazole.

Also included with the invention are pharmaceutically acceptable salts of the above compounds.

The preferred pharmaceutically acceptable salts are the hydrochloride, hydrobromide, nitrate, maleate and citrate, and correspondingly the particularly preferred salts are the corresponding salts of this group of the preferred compounds described above.

Process of Preparation

One process of the invention, can be represented by the following overall reaction equation:

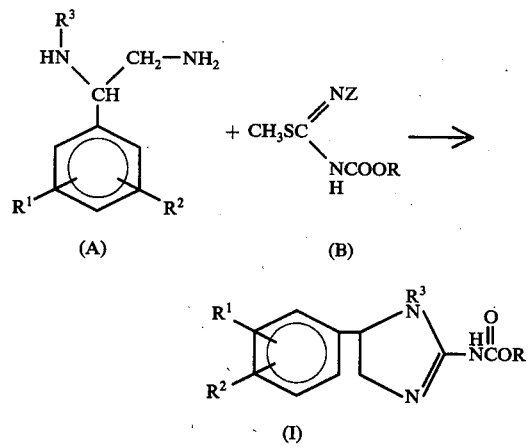

wherein R, $R^1$, $R^2$ and $R^3$ are as defined hereinabove, and Z is hydrogen or the same as the group —COOR. Alternatively, instead of the reagent of formula B the following reagent can be used in a variant of the reaction

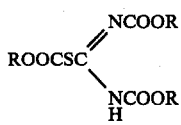
(B')

wherein R is defined as hereinabove.

This reaction or its variant can be conveniently effected by treating the compound of formula A, having the desired $R^1$, $R^2$ and $R^3$ substituent, or typically an acid salt thereof, e.g. the dihydrochloride salt, with the starting material of formula B or B' having the desired R substituent, in a suitable solvent. Typically, the reaction is conducted under alkaline to slightly acid conditions, preferably essentially neutral. Typically, where an acid salt of formula A is used, a sufficient amount of an inorganic or organic base is added to the reaction mixture either before or after the addition of one or both of the reactants to neutralize all or part of the acid salt moiety. Suitable bases which can be used include, for example, alkali metal carbonate, or bicarbonates, acetates, for example, sodium carbonate, potassium carbonate, sodium bicarbonate, sodium acetate, alkali metal lower alkoxides, for example, sodium methoxide, potassium methoxide, sodium t-butoxide, lithium methoxide, and the like, alkali metal and alkali earth hydroxides, for example, sodium hydroxide, potassium hydroxide, calcium hydroxide, and the like, and mixtures thereof. Suitable organic bases include, for example, pyridine, triethylamine, diazabicyclononane, and the like or mixtures thereof.

Conveniently, the solvent in which the reaction is carried out is a mixture of water and one or more inert organic solvents. Suitable inert organic solvents which can be used include, for example, methanol, ethanol, isopropanol, diethyl ether, chloroform, benzene and the like and mixtures thereof. The reaction is carried out at temperatures in the range of about from 10 to 100° C, preferably about from 50° to 75° C, for about from ½ hr. to 14 days. Typically, a mole ratio of about from 0.5 to 2, preferably about 1 mole of starting material A is used per mole of starting material B or B'. However, temperatures, reaction times, and mole ratios both above and below these ranges can be used. Optimum conditions will, of course, vary with the particular reactants and solvents, and can be determined by routine experimentation. The products of formula I can be separated from the product reaction mixture and further purified by conventional procedures, e.g. filtration, washing, evaporation, crystallization and the like. Non-limiting illustrations of detailed separation and purification procedures can be had by reference to the Examples set forth hereinbelow.

The starting materials of formulae B and B' are known compounds and can be prepared according to known procedures such as those set forth in Japanese Application No. 50012087 or, for example, by the procedure described in Example 9 hereinbelow or by obvious modifications of such procedures. The compounds of formula B can be used either as the respective mono- (Z is H) or bis- (Z is COOR) or as a mixture of the mono- and bis- compounds. Conveniently, the compound of formula B is prepared as a mixture of the mono- (Z is H) and bis- (Z is COOR) and the mixture then used in the aforedescribed reaction without separation of the mono- and bis-products.

The starting materials of formula A are readily prepared according to procedures analagous to known procedures, note, for example, the procedures described by W. L. Matier et al in the *Journal of Medicinal Chemistry*, Vol. 16, No. 8, page 901 (1973), and by the procedures described herein in the Preparations, or by obvious modifications of such procedures. Thus, the starting materials of formula A may be prepared according to the following reaction scheme

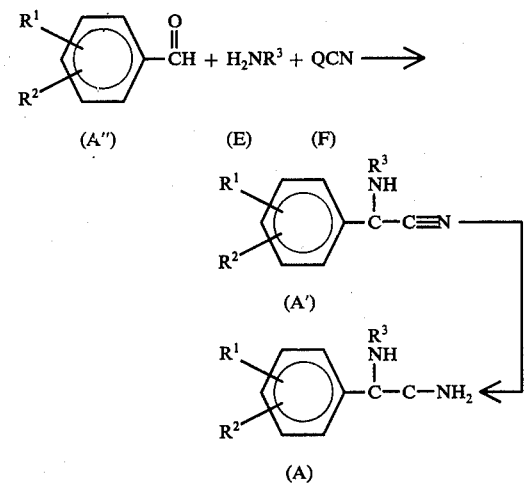

wherein R, $R^1$, $R^2$ and $R^3$ are defined hereinbefore and Q is a metal group such as an alkali metal or an alkaline earth metal. According to this scheme an appropriately substituted benzaldehyde (A'') is reacted with a lower alkyl amine (E) in the presence of a metal cyanide (F) to give the corresponding 2-(substituted or unsubstituted phenyl)-2-lower alkylamino acetonitrile (A'). This in turn is converted to 2-(substituted or unsubstituted phenyl)-2-lower alkyl amino-ethylamine.

In the first step the appropriately substituted benzaldehyde is placed in a suitable solvent along with the alkyl amine or preferably the acid addition salt thereof. Suitable solvents are any solvents in which the reaction can take place and which are substantially inert to the reactant. The solvents include those such as dimethylsulfoxide, acetonitrile, methanol, water and the like. Alkyl amines which can be used in the process include methylamine, ethylamine, isopropylamine, n-propylamine, n-butylamine, t-butylamine, n-pentylamine, isopentylamine, n-hexylamine and the like and their corresponding acid addition salts, such as hydrochlorides, etc.. The metal cyanides which can be used include alkali metal cyanides such as sodium cyanide, potassium cyanide, and the like as well as alkaline earth cyanides such as calcium cyanide, magnesium cyanide, and the like. Because of its ready availability, sodium cyanide is preferred. Typically, the reaction generally takes place at about 10° C to about 40° C, preferably at ambient temperatures, that is about 20° C–25° C. The reaction can be run at higher or lower temperatures but at lower temperatures the reaction continues more slowly while at higher temperatures there are greater yield losses. Generally the reaction can continue for a few hours to several days, generally about 16 hours to 3 days is required to complete the reaction. The acetonitrile (A')

may then be purified by conventional means such as filtration, crystallization, and the like.

Once the acetonitrile is obtained, it is dissolved in a suitable inert solvent such as an oxygenated hydrocarbon, for example ether, tetrahydrofuran, 12-dimethoxyethane, and the like. The acetonitrile is converted to an amine using a suitable reducing agent. Generally this is done using lithium aluminum hydride (LiAlH$_4$) but other suitable reducing agents may also be used. Typically, the reduction is started at a temperature of about −25° to about +15° C preferably about −10° to 10° C but is allowed to warm to ambient temperature as the reaction progresses. Generally the reaction will be completed in a few hours to several days. Generally about 16 to 24 hours will be required for the action to proceed to completion. The β-alkylamino-β-(substituted or unsubstituted phenyl)-ethylamine is then purified by conventional purification methods and utilized to prepare compounds of this invention.

In a further process embodiment, the compounds of the invention can be prepared by treating the compound of formula A with a compound of the general formula

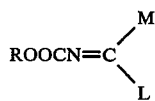

wherein R is as defined hereinabove and M and L independently are chlorine, lower alkoxy or lower alkylthio. The term lower alkoxy or lower alkylthio refers to alkoxy or alkylthio groups having an alkyl group from one through six carbon atoms which may be branched or straight chain attached to an oxygen or sulfur atom. The reaction preferably is carried out in the presence of a suitable organic or inorganic base, such s triethylamine, pyridine, sodium hydroxide, sodium bicarbonate or sodium carbonate at 0° to 100° C, preferably at 0° to 50° C.

If one of M or L is halogen and the other of M or L is lower alkoxy or lower alkylthio the reaction is first started in the presence of a base and completed at a pH of 2 to 8 between 0 to 150° C, preferably 20° to 120° C.

If both M and L are lower alkoxy or lower alkylthio, the reaction is carried out at 0° to 150° C, preferably 30° to 120° C, optionally in a solvent such as a lower alkanol, acetonitrile diluted acetic acid, ethylene glycol, tetrahydrofurane, dioxane, benzene, toluene, halogenated hydrocarbon, water, or the like. It is advantageous to use solvents which contain water. The pH range should be between 2 and 8 preferably between 2 and 5.

The compounds of formula G are known compounds and can be prepared in accordance with the procedures described in German OLS 2438120.

In still a further modification the compounds of the invention can be prepared by treating the compound of formula A with a compound of the general formula

ROOC—NHCN           (H)

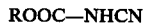

wherein R is as defined above. The reaction conditions are the same as applied with the compounds of the formula G (with M and L both being lower alkoxy or lower alkylthio). The compounds of formula H may also be prepared by methods described in German OLS No. 2438120.

In a further embodiment, the compounds of this invention are prepared by the following overall reaction equation:

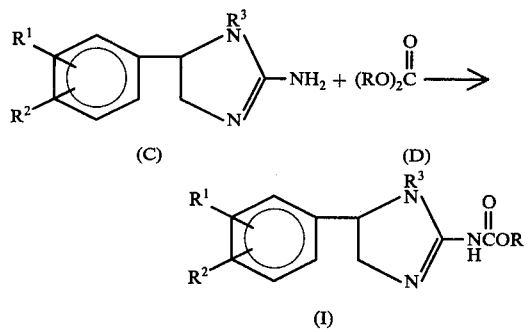

wherein R, R$^1$, R$^2$ and R$^3$ are as defined hereinabove. This reaction can be conveniently effected at a suitable temperature by treating the compound of formula C, having the desired R$^1$ R$^2$ and R$^3$ substituents, or typically an acid salt thereof, e.g. the hydrobromide salt, with the starting material of formula D having the desired R substituent in an inert solvent or by using an excess of compound D as the solvent. A suitable temperature for the reaction will be about 20° C to about 120° C, preferably about 70° C to about 100° C. Typically where an acid salt of compound C is used as the starting material, the salt is treated before addition of compound D with a sufficient amount of an inorganic or organic base to liberate the free base. Suitable bases which can be used include, for example, alkali metal carbonates, alkali metal lower alkoxides, for example, sodium methoxide, potassium methoxide, sodium t-butoxide, lithium methoxide, and the like, alkali metal and alkali earth hydroxides, for example, sodium hydroxide, potassium hydroxide, calcium hydroxide, and the like, and mixtures thereof. Suitable organic bases include, for example, pyridine, triethylamine, diazabicyclononane, and the like and mixtures thereof. Suitable inert organic solvents which can be used include, for example, toluene, dioxane, and the like and mixtures thereof.

The compounds of the invention can also be prepared by reacting the compound of formula C, having the desired R$^1$, R$^2$ and R$^3$ substituents with an alkyl chloroformate (ClCOOR) having the desired R-alkyl substituent in a suitable inert organic solvent; e.g. acetone. This reaction takes place at about −20° C to about 20° C, preferably about −5° C to 5° C.

The starting materials of formula C can be prepared according to methods analogous to known procedures such as, for example, described by Matier et al in the *Journal of Medicinal Chemistry*, Vol. 16, No. 8, page 901 (1973) and the Preparations set forth hereinbelow or obvious modifications of such procedures.

The respective optically active isomers of formula I can be conveniently prepared by using the corresponding optically active isomer starting material of formula A or C in the aforedescribed processes. The optically active isomer starting materials can be obtained by resolution of the corresponding (dl) mixture by applying conventional resolution procedures, note, for example, the procedure described in *Ann. Chem.*, Vol. 494, page 143 (1932).

The pharmaceutically acceptable salts of the invention can be conveniently prepared by treating the corresponding free base of formula I, of the invention, with an acid or via other conventional procedures such as, for example, ion exchange. The free base of formula I may be obtained from the pharmaceutically acceptable salt by treating said salt with a conventional organic or inorganic base such as one employed to liberate a free base of compound C from the corresponding acid salt as described hereinbefore.

Utilities and Administration

The compounds of the invention are useful as psychotropic agents for treating, palliating, or preventing undesirable conditions, in mammals, involving the central nervous system such as depression, anxiety, convulsions and centrally induced skeletal muscle spasm, or spasticity disorders. Initial determination of the spectrum of psychotropic activity, in mammals, for a given compound, can, for example, be obtained by applying routine expermental procedures, for example, for antidepressant activity, Askew, *Life Sciences,* Vol. 2, page 725 (1963) and Vernier et al, *Fed. Proc.,* Vol. 21, page 419 (1962); for depressant or tranquilizing activity, Irwin, "Animal and Clinical Pharmacological Techniques" in *Drug Evaluation,* edited by J. H. Nodine et al, pages 36–54, Yearbook Medical Publishers, Inc., Chicago (1964); for anticonvulsant activity, Swinyard, J. of Amer. Phar. Assoc., Scientific Edition, Vol. 38, page 20 (1941); for centrally acting skeletal muscle relaxant activity (based on polysynaptic transmission inhibition), King and Unna, "The Action of Mephenesin and Other Interneuron Depressants on the Brain Stem", *J. Pharmacol. Exp. Ther.,* Vol. 111, page 293 (1954) and Kamijo and Koelle; Barnett and Fiore; *Europ. J. Pharmacol.,* Vol, 13, p. 239 (1971): *Proceedings of the Society for Experimental Biology in Medicine,* Vol. 88, pages 565–568 (1955).

Judging from determinations based on the results of small animal studies certain compounds are valuable as antidepressants, e.g. the compounds of formula (I) wherein the total number of carbons in R and $R^3$ together is 2 or 3; $R^1$ is hydrogen; and $R^2$ is hydrogen, fluoro, chloro, bromo, iodo, alkyl of 1–3 carbons, trifluoromethyl, hydroxy, or alkoxy of 1–3 carbon atoms. Representative of compounds of this subgroup include 1-methyl-4,5-dihydro-5-phenyl-2-methoxycarbonylaminoimidazole, m.p. 145°–147° C;
1-methyl-4,5-dihydro-5-(2-fluorophenyl)-2-methoxycarbonylaminoimidazole, m.p. 178°–180° C;
1-methyl-4,5-dihydro-5-(3-fluorophenyl)-2-methoxycarbonylaminoimidazole;
1-methyl-4,5-dihydro-5-(4-fluorophenyl)-2-methoxycarbonylaminoimidazole;
1-methyl-4,5-dihydro-5-(2-chlorophenyl)-2-methoxycarbonylaminoimidazole, m.p. 153°–155° C;
1-methyl-4,5-dihydro-5-(3-chlorophenyl)-2-metoxycarbonylaminoimidazole;
1-methyl-4,5-dihydro-5-(4-clorophenyl)-2-methoxycarbonylaminoimidazole, m.p. 184°–186° C;
1-methyl-4,5-dihydro-5-(2-bromophenyl)-2-metoxycarbonylaminoimidazole;
1-methyl-4,5-dihydro-5-(3-bromophenyl)-2-methoxycarbonyaminoimidazole;
1-methyl-4,5-dihydro-5-(4-bromophenyl)-2-methoxycarbonylaminoimidazole;
1-methyl-4,5-dihydro-5-(2-iodophenyl)-2-methoxycarbonylaminoimidazole;
1-methyl-4,5-dihydro-5-(3-iodophenyl)-2-methoxycarbonylaminoimidazole;
1-methyl-4,5-dihydro-5-(3-methylphenyl)-2-methoxycarbonylaminoimidazole, m.p. 158°–16° C;
1-methyl-4,5-dihydro-5-(3-isopropylphenyl)-2-methoxycarbonylaminoimidazole;
1-methyl-4,5-dihydro-5-(4-n-hexylphenyl)-2-methoxycarbonylaminoimidazole;
1-methyl-4,5-dihydro-5-(2-trifluoromethylphenyl)-2-methoxycarbonylaminoimidazole;
1-methyl-4,5-dihydro-5-(2-hydroxyphenyl)-2-methoxycarbonylaminoimidazole;
1-methyl-4,5-dihydro-5-(3-hydroxyphenyl)-2-methoxycarbonylaminoimidazole;
1-methyl-4,5-dihydro-5-(4-hydroxyphenyl)-2-methoxycarbonylaminoimidazole;
1-methyl-4,5-dihydro-5-(2-ethoxyphenyl)-2-methoxycarbonylaminoimidazole;
1-methyl-4,5-dihydro-5-(3-methoxyphenyl)-2-methoxycarbonylaminoimidazole, m.p. 137°–138° C;
1-methyl-4,5-dihydro-5-(4-isopropoxyphenyl)-2-methoxycarbonylaminoimidazole;
1-methyl-4,5-dihydro-5-phenyl-2-ethoxycarbonylaminoimidazole, m.p. 135°–138° C;
1-methyl-4,5-dihydro-5-(2-fluorophenyl)-2-ethoxycarbonylaminoimidazole;
1-methyl-4,5-dihydro-5-(3-fluorophenyl)-2-ethoxycarbonylaminoimidazole;
1-methyl-4,5-dihydro-5-(4-fluorophenyl)-2-ethoxycarbonylaminoimidazole;
1-methyl-4,5-dihydro-5-(2-chlorophenyl)-2-ethoxycarbonylaminoimidazole, m.p. 117°–118° C;
1-methyl-4,5-dihydro-5-(4-bromophenyl)-2-ethoxycarbonylaminoimidazole;
1-methyl-4,5-dihydro-5-(2-methylphenyl)-2-ethoxycarbonylaminoimidazole;
1-methyl-4,5-dihydro-5-(3-ethylphenyl)-2-ethoxycarbonylaminoimidazole;
1-methyl-4,5-dihydro-5-(4-isopropylphenyl)-2-ethoxycarbonylaminoimidazole
1-methyl-4,5-dihydro-5-(4-trifluoromethylphenyl)-2-ethoxycarbonylaminoimidazole;
1-methyl-4,5-dihydro-5-(2-hydroxyphenyl)-2-ethoxycarbonylaminoimidazole;
1-methyl-4,5-dihydro-5-(3-methoxyphenyl)-2-alkoxycarbonylaminoimidazole;
1-methyl-4,5-dihydro-5-(4-ethoxyphenyl)-2-ethoxycarbonylaminoimidazole;
1-ethyl-4,5-dihydro-5-phenyl-2-methoxycarbonylaminoimidazole, m.p. 115°–116° C;
1-ethyl-4,5-dihydro-5-(2-fluorophenyl)-2-methoxycarbonylaminoimidazole;
1-ethyl-4,5-dihydro-5-(3-fluorophenyl)-2-methoxycarbonylaminoimidazole;
1-ethyl-4,5-dihydro-5-(4-fluorophenyl)-2-methoxycarbonylaminoimidazole;
1-ethyl-4,5-dihydro-5-(3-chlorophenyl)-2-methoxycarbonylaminoimidazole;
1-ethyl-4,5-dihydro-5-(2-bromophenyl)-2-methoxycarbonylaminoimidazole;
1-ethyl-4,5-dihydro-5-(2-ethylphenyl-2-methoxycarbonylaminoimidazole;
1-ethyl-4,5-dihydro-5-(2-ethylphenyl)-2-methoxycarbonylaminoimidazole;
1-ethyl-4,5-dihydro-5-(4-methylphenyl)-2-methoxycarbonylaminoimidazole;
1-ethyl-4,5-dihydro-5-(2-trifluoromethylphenyl)-2-methoxycarbonylaminoimidazole;
1-ethyl-4,5-dihydro-5-(3-hydroxyphenyl)-2-methoxycarbonylaminoimidazole;

1-ethyl-4,5-dihydro-5-(4-methoxyphenyl)-2-methoxycarbonylaminoimidazole; and
1-ethyl-4,5-dihydro-5-(3-ethoxyphenyl)-2-methoxycarbonylaminoimidazole.

Still another group showing antidepressant activity includes those represented by formula (I) wherein the total number of carbon atoms in R and $R^3$ taken together is taken from 2 to 7 inclusive; $R^1$ is hydrogen; and $R^2$ is hydrogen, fluoro, chloro or hydroxy. The compounds of this group are represented by certain compounds already named above and by the following:

1-methyl-4,5-dihydro-5-(2-fluorophenyl)-2-isopropoxycarbonylaminoimidazole;
1-methyl-4,5-dihydro-5-(3-fluorophenyl)-2-isopropoxycarbonylaminoimidazole;
1-methyl-4,5-dihydro-5-phenyl-2-isobutoxycarbonylaminoimidazole, m.p. 103°-104° C;
1-methyl-4,5-dihydro-5-(4-fluorophenyl)-2-isopropoxycarbonylaminoimidazole;
1-methyl-4,5-dihydro-5-(2-hydroxyphenyl)-2-isopropoxycarbonylaminoimidazole;
1-methyl-4,5-dihydro-5-(3-hydroxyphenyl)-2-isopropoxycarbonylaminoimidazole;
1-methyl-4,5-dihydro-5-(4-hydroxyphenyl)-2-isopropoxycarbonylaminoimidazole;
1-t-butyl-4,5-dihydro-5-(2-fluorophenyl)-2-ethoxycarbonylaminoimidazole;
1-isobutyl-4,5-dihydro-5-(4-fluorophenyl)-2-methoxycarbonylaminoimidazole;
1-n-butyl-4,5-dihydro-5-(2-hydroxyphenyl)-2-ethoxycarbonylaminoimidazole;
1-isopropyl-4,5-dihydro-5-(2-fluorophenyl)-2-t-butoxycarbonylaminoimidazole;
1-ethyl-4,5-dihydro-5-(2-fluorophenyl)-2-ethoxycarbonylaminoimidazole;
1-methyl-4,5-dihydro-5-(2-chlorophenyl)-2-n-butoxycarbonylaminoimidazole;
1-ethyl-4,5-dihydro-5-(3-chlorophenyl)-2-n-propoxycarbonylaminoimidazole;
1-isopropyl-4,5-dihydro-5-(4-chlorophenyl)-2-ethoxycarbonylaminoimidazole; and
1-t-butyl-4,5-dihydro-5-(2-chlorophenyl)-2-methoxycarbonylaminoimidazole.
1-methyl-4,5-dihydro-5-(2-chlorophenyl)-2-isopropoxycarbonylaminoimidazole;
1-methyl-4,5-dihydro-5-(3-chlorophenyl)-2-isopropoxycarbonylaminoimidazole;
1-methyl-4,5-dihydro-5-(4-chlorophenyl)-2-isopropoxycarbonylaminoimidazole;
1-ethyl-4,5-dihydro-5-(2-chlorophenyl)-2-ethoxycarbonylaminoimidazole;
1-ethyl-4,5-dihydro-5-(3-chlorophenyl)-2-ethoxycarbonylaminoimidazole;
1-ethyl-4,5-dihydro-5-(4-chlorophenyl)-2-ethoxycarbonylaminoimidazole;
1-propyl-4,5-dihydro-5-(3-chlorophenyl)-2-methoxycarbonylaminoimidazole; and
1-isopropyl-4,5-dihydro-5-(2-chlorophenyl)-2-methoxycarbonylaminoimidazole.

Another group exhibiting antidepressant activity includes those compounds represented by formula (I) wherein R and $R^3$ are both methyl, $R^1$ is hydrogen and $R^2$ is alkyl of 4-7 carbon atoms such as 1-methyl-4,5-dihydro-5-(2-isobutylphenyl)-2-methoxycarbonylaminoimidazole;
1-methyl-4,5-dihydro-5-(3-n-pentylphenyl)-2-methoxycarbonylaminoimidazole;
1-methyl-4,5-dihydro-5-(4-n-hexylphenyl)-2-methoxycarbonylaminoimidazole; and the like.

A further group of this invention including compounds with antidepressant activity are represented by formula (I) wherein the total number of carbon atoms in R and $R^3$ is equal to 4; $R^1$ is hydrogen; and $R^2$ is methyl, trifluoromethyl, 2-bromo, 4-bromo, 2-methoxy, 4-methoxy or 2-iodo. Representative compounds include 1-methyl-4,5-dihydro-5-(2-methylphenyl)-2-isopropoxycarbonylaminoimidazole;
1-methyl-4,5-dihydro-5-(4-trifluoromethylphenyl)-2-isopropoxycarbonylaminoimidazole;
1-methyl-4,5-dihydro-5-(4-methylphenyl)-2-isopropoxycarbonylaminoimidazole;
1-methyl-4,5-dihydro-5-(2-trifluoromethylphenyl)-2-isopropoxycarbonylaminoimidazole;
1-ethyl-4,5-dihydro-5-(3-methylphenyl)-2-ethoxycarbonylaminoimidazole;
1-ethyl-4,5-dihydro-5-(4-trifluoromethylphenyl)-2-ethoxycarbonylaminoimidazole;
1-ethyl-4,5-dihydro-5-(4-methylphenyl)-2-ethoxycarbonylamino imidazole;
1-ethyl-4,5-dihydro-5-(2-trifluoromethylphenyl)-2-ethoxycarbonylaminoimidazole;
1-isopropyl-4,5-dihydro-5-(4-methylphenyl)-2-methoxycarbonylaminoimidazole;
1-propyl-4,5-dihydro-5-(3-trifluoromethylphenyl)-2-methoxycarbonylaminoimidazole.

Another group of compounds of the invention which show antidepressant activity includes those compounds represented by formula (I) wherein the total number of carbon atoms in R and $R^3$ together is 2 through 7 and $R^1$ and $R^2$ together are dichloro, difluoro, or dihydroxy. Representative compounds of this group include 1-methyl-4,5-dihydro-5-(2,6-dichlorophenyl)-2-methoxycarbonylaminoimidazole;
1-methyl-4,5-dihydro-5-(2,4-dichlorophenyl)-2-methoxycarbonylaminoimidazole;
1-methyl-4,5-dihydro-5-(3,5-dichlorophenyl)-2-methoxycarbonylaminoimidazole;
1-methyl-4,5-dihydro-5-(3,4-dichlorophenyl)-2-methoxycarbonylaminoimidazole;
1-methyl-4,5-dihydro-5-(2,3-dichlorophenyl)-2-methoxycarbonylaminoimidazole;
1-ethyl-4,5-dihydro-5-(2,6-dichlorophenyl)-2-methoxycarbonylaminoimidazole; and
1-ethyl-4,5-dihydro-5-(2,4-dichlorophenyl)-2-methoxycarbonylaminoimidazole.
1-methyl-4,5-dihydro-5-(2,4-dichlorophenyl)-2-isopropoxycarbonylaminoimidazole;
1-ethyl-4,5-dihydro-5-(2,6-dichlorophenyl)-2-ethoxycarbonylaminoimidazole;
1-n-propyl-4,5-dihydro-5-(2,5-dichlorophenyl)-2-methoxycarbonylaminoimidazole;
1-methyl-4,5-dihydro-5-(2,4-dichlorophenyl)-2-t-butoxycarbonylaminoimidazole,
1-ethyl-4,5-dihydro-5-(2,6-dichlorophenyl)-2-isopropoxycarbonylaminoimidazole;
1-propyl-4,5-dihydro-5-(2,5-dichlorophenyl)-2-ethoxycarbonylaminoimidazole;
1-ethyl-4,5-dihydro-5-(2,6-dichlorophenyl)-2-methoxycarbonylaminoimidazole;

1-methyl-4,5-dihydro-5-(2,4-dichlorophenyl)-2-ethoxycarbonylaminoimidazole;
1-ethyl-4,5-dihydro-5-(3,5-dichlorophenyl)-2-n-butoxycarbonylaminoimidazole
1-ethyl-4,5-dihydro-5-(3,4-dichlorophenyl)-2-n-pentyloxycarbonylaminoimidazole;
1-methyl4,5-dihydro-5-(2,3-dichlorophenyl)-2-n-hexyloxycarbonylaminoimidazole;
1-isopropyl-4,5-dihydro-5-(2,6-dichlorophenyl)-2-ethoxycarbonylaminoimidazole;
1-isopentyl-4,5-dihydro-5-(2,4-dichlorophenyl)-2-ethoxycarbonylaminoimidazole.
1-methyl-4,5-dihydro-5-(3,4-dihydroxyphenyl)-2-n-hexyloxycarbonylaminoimidazole;
1-isopropyl-4,5-dihydro-5-(3,4-dihydroxyphenyl)-2-t-butoxycarbonylaminoimidazole;
1-t-butyl-4,5-dihydro-5-(3,5-dihydroxyphenyl)-2-methoxycarbonylaminoimidazole;
1-ethyl-4,5-dihydro-5-(2,3-dihydroxyphenyl)-2-pentyloxycarbonylaminoimidazole;
1-methyl-4,5-dihydro-5-(2,4-dihydroxyphenyl)-2-n-pentyloxycarbonylaminoimidazole;
1-methyl-4,5-dihydro-5-(2,6-dihydroxyphenyl)-2-methoxycarbonylaminoimidazole;
1-methyl-4,5-dihydro-5-(2,4-dihydroxyphenyl)-2-methoxycarbonylaminoimidazole;
1-methyl-4,5-dihydro-5-(3,5-dihydroxyphenyl)-2-methoxycarbonylaminoimidazole;
1-methyl-4,5-dihydro-5-(3,6-dihydroxyphenyl)-2-methoxycarbonylaminoimidazole;
1-methyl-4,5-dihydro- 5-(2,3-dihydroxyphenyl)-2-methoxycarbonylaminoimidazole;
1-ethyl-4,5-dihydro-5-(2,6-dihydroxyphenyl)-2-methoxycarbonylaminoimidazole; and
1-ethyl-4,5-dihydro-5-(2,4-dihydroxyphenyl)-2-methoxycarbonylaminoimidazole.
1-n-hexyl-4,5-dihydro-5-(2,6-difluorophenyl)-2-methoxycarbonylaminoimidazole;
1-t-butyl-4,5-dihydro-5-(2,4-difluorophenyl)-2-methoxycarbonylaminoimidazole;
1-t-butyl-4,5-dihydro-5-(2,6-difluorophenyl)-2-isopropoxycarbonylaminoimidazole;
1-methyl-4,5-dihydro-5-(2,6-difluorophenyl)-2-methoxycarbonylaminoimidazole;
1-methyl-4,5-dihydro-5-(2,4-difluorophenyl)-2-methoxycarbonylaminoimidazole;
1-ethyl-4,5-dihydro-5-(3,5-difluorophenyl)-2-ethoxycarbonylaminoimidazole;
1-methyl-4,5-dihydro-5-(3,4-difluorophenyl)-2-ethoxycarbonylaminoimidazole;
1-methyl-4,5-dihydro-5-(2,3-difluorophenyl)-2-methoxycarbonylaminoimidazole;
1-ethyl-4,5-dihydro-5-(2,6-difluorophenyl)-2-methoxycarbonylaminoimidazole;
1-ethyl-4,5-dihydro-5-(2,4-difluorophenyl)-2-methoxycarbonylaminoimidazole;
1-methyl-4,5-dihydro-5-(2,3-difluorophenyl)-2-isopropoxycarbonylaminoimidazole;
1-methyl-4,5-dihydro-5-(2,4-difluorophenyl)-2-isobutoxycarbonylaminoimidazole;
1-methyl-4,5-dihydro-5-(2,6-difluorophenyl)-2-isopentoxycarbonylaminoimidazole;
1-methyl-4,5-dihydro-5-(2,4-dihydroxyphenyl-2-isopropoxycarbonylaminoimidazole;
1-methyl-4,5-dihydro-5-(2,5-dihydroxyphenyl)-2-isopropoxycarbonylaminoimidazole;
1-isopropyl-4,5-dihydro-5-(2,4-difluorophenyl)-2-t-butoxycarbonylaminoimidazole; and the like.

Still another group of compounds of this invention having antidepressant activity includes those compounds represented by formula (I) wherein the total number of carbon atoms in R and $R^3$ taken together is 2 through 4 and both $R^1$ and $R^2$ are bromo, with at least one bromo at the ortho position. Compounds included in this group are represented by
1-methyl-4,5-dihydro-5-(2,4-dibromophenyl)-2-methoxycarbonylaminoimidazole;
1-methyl-4,5-dihydro-5-(2,6-dibromophenyl)-2-ethoxycarbonylaminoimidazole;
1-ethyl-4,5-dihydro-5-(2,3-dibromophenyl)-2-methoxycarbonylaminoimidazole; and
1-ethyl-4,5-dihydro-5-(2,6-dibromophenyl)-2-ethoxycarbonylaminoimidazole.

Still another preferred subgroup of compounds of this invention having antidepressant activity includes those compounds of formula I wherein the total number of carbon atoms in R and $R^3$ is between 2 and 6 inclusive, and $R^1$ and $R^2$ are both methoxy, especially where one of the methoxy substituents is at the ortho position. Representative compounds include 1-methyl-4,5-dihydro-5-(2,4-dimethoxyphenyl)-2-n-propyloxycarbonylaminoimidazole;
1-methyl-4,5-dihydro-5-(2,6-dimethoxyphenyl)-2-n-pentyloxycarbonylaminoimidazole;
1-ethyl-4,5-dihydro-5-(3,5-dimethoxyphenyl)-2-t-butoxycarbonylaminoimidazole;
1-n-pentyl-4,5-dihydro-5-(2,4-dimethoxyphenyl)-2-methoxycarbonylaminoimidazole;
1-methyl-4,5-dihydro-5-(3,4-dimethoxyphenyl)-2-methoxycarbonylaminoimidazole;
1-methyl-4,5-dihydro-5-(2,6-dimethoxyphenyl)-2-methoxycarbonylaminoimidazole;
1-methyl-4,5-dihydro-5-(2,4-dimethoxyphenyl)-2-ethoxycarbonylaminoimidazole;
1-ethyl-4,5-dihydro-5-(2,6-dimethoxyphenyl)-2-methoxycarbonylaminoimidazole; and
1-methyl-4,5-dihydro-5(2,4-dimethoxyphenyl)-2-t-butoxycarbonylaminoimidazole.

Still another subgroup of the compounds of this invention which exhibits antidepressant activity are those represented by formula (I) wherein the total number of carbons in R and $R^3$ is 2, 3 or 4 and both $R^1$ and $R^2$ are ethoxy with at least one ethoxy being at the ortho position. Compounds representative of this group are 1-methyl-4,5-dihydro-5-(2,4-diethoxyphenyl)-2-methoxycarbonylaminoimidazole;
1-methyl-4,5-dihydro-5-(2,6-diethoxyphenyl)-2-methoxycarbonylaminoimidazole;
1-ethyl-4,5-dihydro-(2,3-diethoxyphenyl)-2-methoxycarbonylaminoimidazole;
1-ethyl-4,5-dihydro-5-(2,5-diethoxyphenyl)-2-ethoxycarbonylaminoimidazole;
1-methyl-4,5-dihydro-(2,6-diethoxyphenyl)-2-isopropoxycarbonylaminoimidazole; and
1-n-propyl-4,5-dihydro-5-(2,3-diethoxyphenyl)-methoxycarbonylaminoimidazole.

Still another subgroup of compounds of the invention which show antidepressant activity includes those compounds represented by formula (I) wherein the total number of carbon atoms in R and $R^3$ taken together is 2 or 3 and $R^1$ and $R^2$ together are methylenedioxy. For example 1-methyl-4,5-dihydro-5-(2,3-methylenedioxyphenyl)-2-methoxycarbonylaminoimidazole;
1-methyl-4,5-dihydro-5-(3,4-methylenedioxyphenyl)-2-ethoxycarbonylaminoimidazole; and
1-ethyl-4,5-dihydro-5-(2,3-methylenedioxyphenyl)-2-methoxycarbonylaminoimidazole.

Other compounds having antidepressant activity include those wherein the total number of carbons in R and $R^3$ is 2 through 5 and $R^1$ and $R^2$ are both iodo at an ortho position, for example 1-methyl-4,5-dihydro-5-(2,6-diiodophenyl)-2-methoxycarbonylaminoimidazole;
1-methyl-4,5-dihydro-5-(2,6-diiodophenyl)-2-ethoxycarbonylaminoimidazole;
1-ethyl-4,5-dihydro-5-(2,6-diiodophenyl)-2-methoxycarbonylaminoimidazole; and the like.

Another group of compounds of the invention having antidepressant activity include those represented by formula (I) wherein the total number of carbons in R and $R^3$ is 2 or 3 and $R^1$ and $R^2$ are both methyl, for example 1-methyl-4,5-dihydro-5-(2,5-dimethylphenyl)-2-ethoxycarbonylaminoimidazole;
1-ethyl-4,5-dihydro-5-(2,5-dimethylphenyl)-2-methoxycarbonylaminoimidazole;
1-methyl-4,5-dihydro-5-(3,4-dimethylphenyl)-2-ethoxycarbonylaminoimidazole;
1-ethyl-4,5-dihydro-5-(3,4-dimethylphenyl)-2-methoxycarbonylaminoimidazole;
1-methyl-4,5-dihydro-5-(2,3-dimethylphenyl)-2-ethoxycarbonylaminoimidazole;
1-methyl-4,5-dihydro-5-(2,3-dimethylphenyl)-2-methoxycarbonylaminoimidzole;
1-methyl-4,5-dihydro-5-(3,5-dimethylphenyl)-2-ethoxycarbonylaminoimidazole;
1-ethyl-4,5-dihydro-5-(3,5-dimethylphenyl)-2-methoxycarbonylaminoimidazole; and the like.

Other compounds having antidepressant activity include compounds of formula (I) wherein the total number of carbon atoms in R and $R^3$ taken together is 4 and

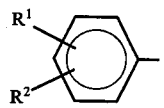

is 2-bromophenyl, 4-bromophenyl, 2-iodophenyl; 2-methylphenyl, 3-methylphenyl, 2-methoxyphenyl, and 4-methoxyphenyl; compounds of formula (I) wherein the total number of carbon atoms in R and $R^3$ taken together is 5 and

is chosen from the group consisting of 2-bromophenyl, 3-ethylphenyl, 2-methoxyphenyl, 4-methoxyphenyl, 2,6-dibromophenyl, 2,5-dimethylphenyl, 2,5-dibromophenyl, 2,3-dibromophenyl, 2,5-dimethylphenyl, 3,5-dimethylphenyl, 2-iodophenyl, 4-ethylphenyl, and 4-ethoxyphenyl; compounds of formula I wherein the total number of carbon atoms in R and $R^3$ taken together is 6, $R^1$ is hydrogen, and $R^2$ is 2-methoxy, compounds of formula I wherein the total number of carbon atoms in R and $R^3$ taken together is 7 and

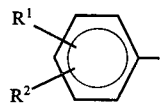

is 2,6-dimethoxyphenyl.

Compounds of formula (I) which exhibit depressant or tranquilizing activity include those wherein $R^1$ is hydrogen; $R^2$ is hydrogen, halo, trifluoromethyl, alkyl of 1–6 carbons, hydroxy, or alkoxy of 1–6 carbons at any position on the phenyl ring; and the total number of carbon atoms in R and $R^3$ together is 2 through 7. Representative compounds falling within this group have been named hereinbefore and will be apparent to one of skill in the art. Other representative compounds include the following:

1-methyl-4,5-dihydro-5-(2-chlorophenyl)-2-n-hexyloxycarbonylaminoimidazole;
1-n-butyl-4,5-dihydro-5-(3-chlorophenyl)-2-isopropoxycarbonylaminoimidazole;
1-ethyl-4,5-dihydro-5-(2-iodophenyl)-2-isopentylcarbonylaminoimidazole;
1-ethyl-4,5-dihydro-5-(3-isopropoxyphenyl)-2-isopropoxycarbonylaminoimidazole;
1-methyl-4,5-dihydro-5-(4-n-propoxyethylphenyl)-2-n-hexyloxycarbonylaminoimidazole;
1-methyl-4,5-dihydro-5-(3-t-butoxyphenyl)-2-methoxycarbonylaminoimidazole;
1-isopropyl-4,5-dihydro-5-(2-n-butoxyphenyl)-2-isopropoxycarbonyl-aminoimidazole;
1-methyl-4,5-dihydro-5-(4-n-pentoxyphenyl)-2-ethoxycarbonylaminoimidazole;
1-ethyl-4,5-dihydro-5-(3-trifluoromethylphenyl)-2-isobutoxycarbonylaminoamidazole;
1-n-propyl-4,5-dihydro-5-(4-methylphenyl)-2-isobutoxycarbonylaminoamidazole;
1-n-pentyl-4,5-dihydro-5-(2-ethylphenyl)-2-methoxycarbonylaminoamidazole;
1-ethyl-4,5-dihydro-5-(4-n-hexylphenyl)-2-isopropoxycarbonylaminoimidazole;
1-methyl-4,5-dihydro-5-(4-isohexylphenyl)-2-ethoxycarbonylaminoimidazole; and the like.

Another group of compounds which exhibit depressant or tranquilizing activity include those of formula (I) wherein the total number of carbon atoms in R and $R^3$ taken together is from 2 to 7, inclusive; $R^1$ is fluoro, chloro, bromo, iodo, hydroxy, alkoxy of 1–6 carbons, or alkyl of 1–6 carbons; $R^2$ is the same as $R^1$, and $R^1$ and $R^2$ are at the 2,5- or 2,3- positions. Compounds representative of this subgroup include certain of the disubstituted phenyl compounds named hereinbefore as well as 1-methyl-4,5-dihydro-5-(2,5-diiodophenyl)-2-ethoxycarbonylaminoimidazole;

1-methyl-4,5-dihydro-5-(2,5-dibromophenyl)-2-n-hexyloxycarbonylaminoimidazole;

1-methyl-4,5-dihydro-5-(2,3-diiodophenyl)-2-methoxycarbonylaminoimidazole;

1-methyl-4,5-dihydro-5-(2,3-diisopropoxyphenyl)-2-methoxycarbonylaminoimidazole;

1-methyl-4,5-dihydro-5-(2,5-di-t-butoxyphenyl)-2-methoxycarbonylaminoimidazole;

1-methyl-4,5-dihydro-5-(2,3-dipentyloxyphenyl)-2-ethoxycarbonylaminoimidazole;

1-ethyl-4,5-dihydro-5-(2,5-di-n-hexyloxyphenyl)-2-methoxycarbonylaminoimidazole;

1-ethyl-4,5-dihydro-5-(2,5-di-trifluoromethylphenyl)-2-methoxycarbonylaminoimidazole;

1-methyl-4,5-dihydro-5-(2,3-di-trifluoromethylphenyl)-2-isopropoxycarbonylaminoimidazole;

1-methyl-4,5-dihydro-5-(2,3-dimethylphenyl)-2-t-butoxycarbonylaminoimidazole;

1-ethyl-4,5-dihydro-5-2,3-dimethylphenyl)-2-isobutoxycarbonylaminoimidazole;

1-isobutyl-4,5-dihydro-5-(2,5-diethylphenyl)-2-isopropoxycarbonylaminoimidazole;

1-isopropyl-4,5-dihydro-5-(2,3-di-isopropylphenyl)-2-t-butoxycarbonylaminoimidazole;

1-t-butyl-4,5-dihydro-5-(2,5-dipentylphenyl)-2-ethoxycarbonylaminoimidazole;

1-methyl-4,5-dihydro-5-(2,5-di-n-hexylphenyl)-2-ethoxycarbonylaminoimidazole;

1-n-propyl-4,5-dihydro-5-(2,5-diisohexylphenyl)-t-butoxycarbonylaminoimidazole.

Certain compounds of this invention exhibit anticonvulsant activity. These compunds include those represented by formula (I) wherein $R^1$ is hydrogen and (i) wherein the total number of carbons in R and $R^3$ together is 2 through 7 and $R^2$ is fluoro or hydrogen;

(ii) wherein the total number of carbons in R and $R^3$ together is 2–4 and $R^2$ is chloro;

(iii) wherein the total number of carbons in R and $R^3$ together is 2–4 and $R^2$ is iodo at the ortho position;

(iv) wherein the total number of carbons in R and $R^3$ together is 4, 6 or 7 $R^2$ is hydroxy, preferably at the ortho or meta position;

(v) wherein the total number of carbons in R and $R^3$ together is 4 or 5 and $R^2$ is methoxy;

(vi) wherein the total number of carbons in R and $R^3$ together is 4 or 5 and $R^2$ is ethoxy at the ortho or para position;

(vii) wherein the total number of carbons in R and $R^3$ together is 2–4 and $R^2$ is methyl;

(viii) wherein the total number of carbons in R and $R^3$ together is 7 and $R^2$ is para methoxy;

(ix) wherein the total number of carbons in R and $R^3$ together is 2–4 and $R^2$ is ethyl at the ortho or para position; and (x) wherein R and $R^3$ are both methyl and $R^2$ is para n-propyl or isopropyl.

Other compounds of this invention which exhibit anticonvulsant activity include compounds represented by formula (I) wherein (i) the total number of carbon atoms in R and $R^3$ together is 5–7 and $R^1$ and $R^2$ are both fluoro;

(ii) the total number of carbon atoms in R and $R^3$ together is 2 or 3 and $R^1$ and $R^2$ are both chloro with at least one chloro at the ortho position;

(iii) the total number of carbon atoms in R and $R^3$ is 2–4 and $R^1$ and $R^2$ are both bromo at an ortho position (i.e. 2,6-dibromo).

(iv) the total number of carbon atoms in R and $R^3$ is 2 or 3 and $R^1$ and $R^2$ are both iodo at an ortho position;

(v) the total number of carbon atoms in R and $R^3$ together is 4–7 and $R^1$ and $R^2$ are both hydroxy, preferably with $R^1$ at an ortho position;

(vi) the total number of carbon atoms in R and $R^3$ together is 4–7 and $R^1$ and $R^2$ are both methoxy at the 2,4- or 2,6- positions;

(vii) the total number of carbon atoms in R and $R^3$ together is 3–6 and $R^1$ and $R^2$ are both ethoxy at an ortho position;

(viii) the total number of carbon atoms in R and $R^3$ is 3 or 4 and $R^1$ and $R^2$ are 2,4-diethoxy;

(ix) R and $R^3$ are both methyl and $R^1$ and $R^2$ are both methyl at the 2,3-, 2,5- or 3,5 positions; and (x) the total number of carbon atoms in R and $R^3$ is 3 and $R^1$ and $R^2$ are both methyl at a meta position (i.e. 3,5-dimethyl).

Representative compounds of this invention showing anticonvulsant activity include 1-methyl-4,5-dihydro-5-(2-chlorophenyl)-2-methoxycarbonylaminoimidazole;

1-methyl-4,5-dihydro-5-phenyl-2-methoxycarbonylaminoimidazole;

1-methyl-4,5-dihydro-5-(2-fluorophenyl)-2-methoxycarbonylaminoimidazole;

1-methyl-4,5-dihydro-5-(2-methylphenyl)-2-methoxycarbonylaminoimidazole;

1-methyl-4,5-dihydro-5-(4-chlorophenyl)-2-methoxycarbonylaminoimidazole;

1-methyl-4,5-dihydro-5-phenyl-2-ethoxycarbonylaminoimidazole;

1-methyl-4,5-dihydro-5-(3-methoxyphenyl)-2-methoxycarbonylaminoimidazole;

1-ethyl-4,5-dihydro-5-phenyl-2-methoxycarbonylaminoimidazole;

1-methyl-4,5-dihydro-5-(3-methylphenyl)-2-methoxycarbonylaminoimidazole; and 1-methyl-4,5-dihydro-5-phenyl-2-isobutoxycarbonylaminoimidazole.

Certain compounds of the invention also show centrally induced muscle relaxant activity. These compounds include 1-methyl-4,5-dihydro-5-(2-chlorophenyl)-2-methoxycarbonylaminoimidazole;

1-methyl-4,5-dihydro-5-(2-methylphenyl)-2-methoxycarbonylaminoimidazole;

1-methyl-4,5-dihydro-5-(4-chlorophenyl)-2-methoxycarbonylaminoimidazole;

1-methyl-4,5-dihydro-5-(3-methylphenyl)-2-methoxycarbonylaminoimidazole; and 1-methyl-4,5-dihydro-5-phenyl-2-isobutoxycarbonylaminoimidazole.

As will be appreciated from the above discussion, a number of the compounds exhibit a mixed spectrum of activities and thus one compound may have more than one utility. Such a mixed spectrum of activities is now recognized to be especially desirable in treating some psychotropic disorders, since such disorders are seldom a consequence of a single abnormality or cause. For example, based on small animal tests, 1-methyl-4,5-dihydro-5-(2-methylphenyl)-2-methoxycarbonylaminoimidazole and 1-methyl-4,5-dihydro-5-(2-chlorophenyl)-methoxycarbonylaminoimidazole exhibit a desirable combination of potent antidepressant activity and moderate to mild depressant activity, and in addition also exhibit some anticonvulsant activity. On the other hand, 1-methyl-4,5-dihydro-5-phenyl-2-methoxycarbonylaminoimidazole and 1-methyl-4,5-dihydro-5-(2-fluorophenyl)-2-methoxycarbonylaminoimidazole exhibit potent antidepressant activity but exhibit less muscle relaxant or anticonvulsant activity.

In general, the preferred dosage depends upon the particular subject and disorder being treated and can vary within wide limits such as, for example, between 0.01 and 300 mg. per kg. of body weight per day. Generally, where the compounds are administered as antidepessants, they can be administered in the same manner as imipramine and preferably are administered at a rate of less than about 50 mg/kg per day. Where the compounds are administered as anticonvulsants, they are best administered prophylactically to prevent or reduce the occurrence and/or severity of convulsions in mammals which are subject to convulsions which are etiopathic to the central nervous system. The compounds can be administered orally, rectally or parenterally (for example, by intravenous, intraperitoneally or intramuscular injection). Where the compounds are administered parenterally, they will, of course, be administered in liquid dosage forms, whereas when administered orally or rectally, they can be administered in either solid or liquid forms. Typically, the dosage forms comprise the compounds in a pharmaceutically acceptable carrier, preferably formulated in unit dosage form to facilitate the simple administration of precise dosages. The dosage form can optionally contain other compatible medicaments and preservatives, emulsifying agents and wetting agents and buffering agents. Liquid dosage forms include, for example, solutions, suspensions, emulsions, syrups, elixirs, etc. Liquid carriers include, for example, water, saline solution, etc. Solid dosage forms include, for example, tablets, powders, capsules, pills, etc. Suitable solid carriers include, for example, pharmaceutical grades of starch, lactose, sodium saccharin, sodium bisulfite and the like, and conventional suppository carriers, e.g. polyethylene glycol, polysorbate, stearic acid, diglycol stearate, carbowax, etc.

DEFINITIONS

The following terms, as used hereinabove and below, have the following meaning unless expressly stated to the contrary. The term lower alkyl refers to alkyls having from one through six carbon atoms and includes both straight chain and branched chain alkyls such as, for example, methyl, ethyl, isopropyl, t-butyl, pentyl, n-hexyl, isohexyl, and the like. The term lower alkoxy refers to alkoxy groups having from one through six carbon atoms and can be defined as the group —OR' wherein R' is lower alkyl as defined hereinabove. The term halo refers to the group of fluoro, chloro, bromo, and iodo. The term pharmaceutically acceptable salts refers to those salts of the parent compound which do not significantly adversely affect the pharmaceutical properties (e.g. toxicity, effectiveness, etc.) of the parent compound such as, for example, are conventionally used in the pharmaceutical art. The pharmaceutically acceptable salts of the present invention are pharmaceutically acceptable hydrogen-anion addition salts of the compounds of formula I. Suitable pharmaceutically acceptable hydrogen-anion addition salts include (expressed with respect to the anion), for example, inorganic salts such as, for example, chloride, bromide, iodide, sulfate, phosphate, nitrate, and the like, or organic salts such as, for example, acetate, benzoate, lactate, propionate, butyrate, valerate, tartrate, maleate, fumarate, citrate, succinate, tosylate, ascorbate, palmitate, glyconate, adipate, and the like.

The term room temperature refers to about 20° Centigrade and all temperatures and temperature ranges refer to degrees centigrade. All percents refer to weight percents and the term equivalent mole amount refers to an amount stoichiometrically equivalent to the other reactant in the reaction referred to.

A further understanding of the invention can be had from the following non-limiting Preparations and Examples; wherein unless expressly stated to the contrary, racemates are used as starting materials and correspondingly racemic mixtures are obtained as products.

PREPARATION I

A. Preparation of
β-methylamino-β-(2-chlorophenyl)-ethylamine, dihydrochloride

A mixture containing 50 milliliters (ml) of dimethylsulfoxide, 15 ml of water, 29 grams (g) of 2-chlorobenzaldehyde, 15 g of methylaminehydrochloride and 12.5 g of sodium cyanide is stirred at room temperature for approximately 76 hours. The reaction mixture is then diluted with water and extracted with benzene. The benzene extract is washed several times with water and then dried over potassium carbonate. Filtration and evaporation of the filtrate under reduced pressure yields crude 2-(2-chlorophenyl)-2-methylaminoacetonitrile. This material is dissolved in approximately 100 ml of ether and added to a solution of 13 g of lithium aluminum hydride in 300 ml of ether. The reaction temperature is kept between −10° and 5° C at first and is then allowed to warm to room temperature. After stirring for about 20 hours there is added cautiously and dropwise first 13 ml of water, then 13 ml of 15% sodium hydroxide and finally 20 ml of water. The mixture is stirred until the solid is nearly white and the solid is then removed by filtration.

When a mixture of 40 ml of concentrated hydrochloric acid and 200 ml of isopropanol is added to the filtrate there is separation of an oily precipitate. Scratching with a glass rod and occasional stirring causes the product, β-methylamino-β-(2-chlorophenyl)-ethylamine dihydrochloride to solidify. (29.2 g, m.p. 258°–262°). Recrystallization from ethanol does not change the melting point.

Similarly, by following the same procedure but using the corresponding benzaldehyde or substituted benzaldehyde as starting material in place of 2-chlorobenzaldehyde and the corresponding alkyl amine hydrochloride for methylamine hydrochloride the dihydrochloride salts of the following compounds are respectively prepared.

β-isopropyl-β-(4-fluorophenyl)-ethylamine;
β-ethylamine-β-(3-fluorophenyl)-ethylamine;
β-methylamino-β-(2-fluorophenyl)-ethylamine; m.p. dihydrochloride 235°–37° C;
β-methylamine-β-(3-chlorophenyl)-ethylamine;
β-methylamine-β-(4-chlorophenyl)-ethylamine; m.p. dihydrochloride 250°–53° C;
β-isobutylamino-β-(3-chlorophenyl)-ethylamine;
β-n-hexylamino-β-(2-bromophenyl)-ethylamine;

β-isopentylamino-β-(4-bromophenyl)-ethylamine;
β-methylamino-β-(3-iodophenyl)-ethylamine;
β-ethylamino-β-(4-iodophenyl)-ethylamine;
β-methylamino-β-(4-trifluoromethylphenyl)-ethylamine;
β-isopropylamino-β-(2-trifluoromethylphenyl)-ethylamine;
β-t-butylamino-β-(3-trifluoromethylphenyl)-ethylamine;
β-t-pentylamino-β-(4-methylphenyl)-ethylamine;
β-n-hexylamino-β-(3-methylphenyl)-ethylamine;
β-methylamino-β-(2-methylphenyl)-ethylamine; b.p. 125°–130° C/25 mm;
β-ethylamino-β-(2-ethylphenyl)-ethylamine;
β-n-butylamino-β-(3-ethylphenyl)-ethylamine;
β-n-pentylamino-β-(4-ethylphenyl)-ethylamine;
β-methylamino-β-(4-t-butylphenyl)-ethylamine;
β-ethylamino-β-(2-t-butylphenyl)-ethylamine;
β-methylamino-β-(4-hexylphenyl)-ethylamine;
β-isopropylamino-β-(3-hexylphenyl)-ethylamine;
β-ethylamino-β-(4-methoxyphenyl)-ethylamine;
β-methylamino-β-(3-methoxyphenyl)-ethylamine; m.p. dihydrochloride 239°–41° C;
β-isohexylamino-β-(2-methoxyphenyl)-ethylamine;
β-t-pentylamino-β-(2-ethoxyphenyl)-ethylamine;
β-methylamino-β-(3-ethoxyphenyl)-ethylamine;
β-methylamino-β-(3-methylphenyl)-ethylamine; m.p. dihydrochloride 202°–205° C; β-n-butylamino-β-(4-ethoxyphenyl)-ethylamine;
β-methylamino-β-(4-isopropoxyphenyl)-ethylamine;
β-ethylamino-β-(3-t-butoxyphenyl)-ethylamine;
β-methylamino-β-(3-pentoxyphenyl)-ethylamine;
β-methylamino-β-(2-hydroxyphenyl)-ethylamine;
β-ethylamino-β-(3-hydroxyphenyl)-ethylamine;
β-n-hexylamino-β-(4-hydroxyphenyl)-ethylamine;
β-methylamino-β-(2,3-dimethylphenyl)-ethylamine;
β-ethylamino-β-(2,4-dimethylphenyl)-ethylamine;
β-isopropylamino-β-(2,5-dimethylphenyl)-ethylamine;
β-n-propylamino-β-(2,6-dimethylphenyl)-ethylamine;
β-t-butylamino-β-(3,4-diethylphenyl)-ethylamine;
β-n-butylamino-β-(3,5-diethylphenyl)-ethylamine;
β-methylamino-β-(3,4-di-t-butylphenyl)-ethylamine;
β-isobutylamino-β-(2,6-di-t-butylphenyl)-ethylamine;
β-n-pentylamino-β-(3,5-diisobutylphenyl)-ethylamine;
β-methylamino-β-(2,5-di-n-hexylphenyl)-ethylamine;
β-ethylamino-β-(2,4-di-n-hexylphenyl)-ethylamine;
β-isopentylamino-β-(3,4-di-n-hexylphenyl)-ethylamine;
β-t-pentylamino-β-(2,4-dihydroxyphenyl)-ethylamine;
β-n-hexylamino-β-(2,3-dimethoxyphenyl)-ethylamine;
β-3-hexylamino-β-(2,5-dimethoxyphenyl)-ethylamine;
β-methylamino-β-(2,6-dimethoxyphenyl)-ethylamine;
β-ethylamino-β-(3,5-dimethoxyphenyl)-ethylamine;
β-t-butylamino-β-(2,5-diisopropoxyphenyl)-ethylamine;
β-isoproprylamino-β-(2,4-diisopropoxyphenyl)-ethylamine;
β-methylamino-β-(3,4-diisopropoxyphenyl)-ethylamine
β-ethylamino-β-(2,6-di-n-hexoxyphenyl)-ethylamine;
β-methylamino-β-(3,4-di-hexoxyphenyl)-ethylamine;
β-n-hexylamino-β-(2,5-di-n-hexoxyphenyl)-ethylamin;
β-methylamino-β-(2,3-difluorophenyl)-ethylamine;
β-ethylamino-β-(2,4-difluorophenyl)-ethylamine;
β-methylamino-β-(2,5-difluorophenyl)-ethylamine;
β-isobutylamino-β-(2,6-difluorophenyl)-ethylamine;
β-n-pentylamino-β-(3,4-difluorophenyl)-ethylamine;
β-n-hexylamino-β-(3,5-difluorophenyl)-ethylamine;
β-methylamino-β-(2,3-dichlorophenyl)-ethylamine;
β-ethylamino-β-(2,5-dichlorophenyl)-ethylamine; and
β-isopropylamino-β-(2,6-dichlorophenyl)-ethylamine.

PREPARATION II

Preparation of β-ethylamino-β-phenyl ethylamine, dihydrochloride

A mixture consisting of 35 ml of acetonitrile; 10 ml of water; 16.8 g of benzaldehyde; 16 g of ethylamine hydrochloride and 10 g of sodium cyanide is stirred at room temperature for 2 days. It is then diluted with more water and extracted with benzene. The benzene extract is washed several times in the water and then dried over potassium carbonate. The solution is filtered and the filtrate is concentrated under reduced pressure to leave crude 2-ethylamino-2-phenylacetonitrile. This material is reduced with 11.5 g of lithium aluminum hydride in ether, following the procedure and workup already described. There is 10.7 g of β-ethylamino-2-phenylethylamine, dihydrochloride, m.p. 226°–229° C.

Similarly, by following the same procedure but using corresponding alkyl amine hydrochlorides, other dihydrochloride salts are respectively prepared such as β-methylamino-β-phenylethylamine; m.p. dihydrochloride 242°–44° C;
β-isopropylamino-β-phenylethylamine;
β-n-hexylamino-β-phenylethylamine; and the like.

PREPARATION III

Preparation of 1-methyl-4,5-dihydro-5-(2-chlorophenyl)-2-aminoimidazole, hydrobromide salt A mixture consisting of 2.5 g. of β-methylamino-β-(2-chlorophenyl)-ethylamine, dihydrochloride and 1.08 g. of sodium methoxide is stirred in 80 ml. of ethanol for 15 minutes. The insoluble material is removed by filtration and is added to the filtrate. A solution of 1.06 g, of cyanogen bromide in 20 ml. of ethanol is added. The clear solution is allowed to stand at room temperature for 2 hours and is then concentrated to dryness by evaporation under reduced pressure. The remaining solid is recrystallized from 50 ml. of isopropanol and the white crystalline product is collected and dried at 55° C under vacuum to give 1.76 g. of 1-methyl-4,5-dihydro-5-(2-chlorophenyl)-2-aminoimidazole, hydrobromide salt; m.p. 250°–251° C.

Similarly, by following the same procedure but using other corresponding β-alkylamino-β-(substituted or unsubstituted phenyl)-ethylamines in place of β-methylamino-β-(2-chlorophenyl)-ethylamine other hydrobromide salts of the following compounds may be obtained:

1-ethyl-4,5-dihydro-5-(2-fluorophenyl)-2-aminoimidazole;
1-isopropyl-4,5-dihydro-5-(3-bromophenyl)-2-aminoimidazole;
1-t-butyl-4,5-dihydro-5-(2-hydroxyphenyl)-2-aminoimidazole;
1-n-hexyl-4,5-dihydro-5-(4-fluorphenyl)-2-aminoimidazole;
1-methyl-4,5-dihydro-5-(4-methylphenyl)-2-aminoimidazole;
1-methyl-4,5dihydro-5-(4-n-hexylphenyl)-2-aminoimidazole;
1-methyl-4,5-dihydro-5-(2-methoxyphenyl)-2-aminoimidazole;

1-ethyl-4,5-dihydro-5-(3-trifluoromethylphenyl)-2-aminoimidazole; and other
1-alkyl-4,5-dihydro-5-(mono- or disubstituted or unsubstituted phenyl)-2-aminoimidazoles.

EXAMPLE 1

A. This example illustrates methods according to the invention of preparing the compounds of the invention having an unsubstituted or alkyl substituted phenyl group. In this example, 30 ml. of ethanol containing 4 ml. of water and 2.5 g. of β-methylamino-β-(2-methylphenyl)-ethylamine is stirred and a solution containing 2.2 g. of a mixture of 1-mono- and 1,3-bis-(methoxycarbonyl)-S-methylisothiourea in 20 ml. of chloroform is added and then stirred for about ten days at room temperature. The mixture is then concentrated by evaporation to near dryness and the solid residue is swirled with water, collected, and stirred in 25 ml. of aqueous 1 Normal hydrochloric acid for one hour. The resulting mixture is washed with ethyl ether, then treated with aqueous sodium bicarbonate and filtered. The collected solid is then stirred with distilled water, refiltered and washed in this manner three more times, then dried overnight at room temperature affording 3.6 g. of product, m.p. 158°–160° C. Recrystallization from benzene-hexane affords 1-methyl-4,5-dihydro-5-(2-methylphenyl)-2-methoxycarbonylaminoimidazole, m.p. 158°–161° C.

The hydrochloride salt is prepared by dissolving the free base in some ethanol that contains about 1 g. of hydrogen chloride. This solution is slightly warmed and ether is added under stirring until the solution is slightly cloudy. Crystallization of the pure hydrochloride salt is induced by occasional scratching with a glass rod; m.p. 144°–146° C.

B. Similarly, by following the same procedure of part A but using the corresponding alkyl substituted phenyl or unsubstituted phenyl-β-methylamino-ethylamine starting materials in place of β-methylamino-β-(2-methylphenyl)-ethylamine, the following compounds are respectively prepared:

1-methyl-4,5-dihydro-5-phenyl-2-methoxycarbonylaminoimidazole; m.p. 145°–147° C; as hydrochloride 147°–149° C;
1-methyl-4,5-dihydro-5-(4-methylphenyl)-2-methoxycarbonylaminoimidazole;
1-methyl-4,5-dihydro-5-(3-methylphenyl)-2-methoxycarbonylaminoimidazole; m.p. 175°–177° C;
1-methyl-4,5-dihydro-5-(3-ethylphenyl)-2-methoxycarbonylaminoimidazole;
1-methyl-4,5-dihydro-5-(4-ethylphenyl)-2-methoxycarbonylaminoimidazole;
1-methyl-4,5-dihydro-5-(4-t-butylphenyl)-2-methoxycarbonylaminoimidazole;
1-methyl-4,5-dihydro-5-(2-t-butylphenyl)-2-methoxycarbonylaminoimidazole;
1-methyl-4,5-dihydro-5-(2-hexylphenyl)-2-methoxycarbonylaminoimidazole;
1-methyl-4,5-dihydro-5-(3-hexylphenyl)-2-methoxycarbonylaminoimidazole; and
1-methyl-4,5-dihydro-5-(4-hexylphenyl)-2-methoxycarbonylaminoimidazole;

C. Similarly, by following the same procedure but respectively replacing the 1-mono and 1,3-bis(methoxycarbonyl)-S-methylisothiourea mixture with, e.g. the following mixtures 1-mono and 1,3-bis(ethoxycarbonyl)-S-methylisothiourea; 1-mono and 1,3-bis-(isobutoxycarbonyl)-S-methylisothiourea; and 1-mono-1,3-bis(n-pentoxycarbonyl)-S-methylisothiourea the corresponding 2-ethoxycarbonylamino (e.g. 1-methyl-4,5-dihydro-5-phenyl-2-ethoxycarbonylaminoimidazole, m.p. 135°–138° C), 2-isobutoxycarbonylamino (e.g. 1-methyl-4,5-dihydro-5-phenyl-2-isobutoxycarbonylaminoimidazole; m.p. 103°–104° C) and 2-n-pentoxycarbonylamino derivatives of each of the above compounds are respectively prepared.

D. Similarly, by following the same procedure of part A but respectively replacing the β-methylamino-β-(2-methylphenyl)-ethylamine with other β-alkylamino-β-phenylethylamino or β-alkylamino-(substituted phenyl)-ethylamino such as β-ethylamino-β-phenylethylamine β-isopropylamino-β-(substituted phenyl)-ethylamine, β-t-butylamino-β-(substituted phenyl)-ethylamine, β-isoamylamino-β-(substituted phenyl)-ethylamine, β-2'-t-butylethylamino-β-(substituted phenyl)-ethylamine, or β-n-hexylamino-β-(substituted phenyl)-ethylamine, the corresponding 1-alkyl-4,5-dihydro-5-(substituted phenyl)-2-methoxycarbonylaminoimidazole or 1-alkyl-4,5-dihydro-5-phenyl-2-methoxycarbonylaminoimidazoles such as 1-ethyl-4,5-dihydro-5-phenyl-2-methoxycarbonylaminoimidazole, m.p. 115°–116° C;

1-isopropyl-4,5-dihydro-5-(substituted phenyl)-2-methoxycarbonylaminoimidazole;
1-t-butyl-4,5-dihydro-5-(substituted phenyl)-2-methoxycarbonylaminoimidazole;
1-isoamyl-4,5-dihydro-5-(substituted phenyl)-2-methoxycarbonylaminoimidazole;
1-(2-t-butylethyl)-4,5-dihydro-5-(substituted phenyl)-2-methoxycarbonylaminoimidazole;
1-n-hexyl-4,5-dihydro-5-(substituted phenyl)-2-methoxycarbonylaminoimidazole.

Similarly, by following the procedure of part C of this example, other corresponding 2-alkoxycarbonylaminoimidazoles of the "1-alkyl" compounds represented above may be prepared.

EXAMPLE 2

A. This example illustrates methods according to the invention of preparing the compounds of the invention having an alkoxyphenyl or hydroxyphenyl group at the 5-position. In this example, 50 ml. of isopropanol and a few ml. of saturated sodium bicarbonate is added to a solution containing 3.0 g. of the dihydrochloride salt of β-methylamino-β-(3-methoxyphenyl)-ethylamine dissolved in 10 ml. of water. The mixture is stirred for 15 minutes and then a solution containing 3.0 g. of a mixture of 1-mono and 1,3-bis(methoxycarbonyl)-S-methylisothiourea in 50 ml. of chloroform is added and then stirred for about four days at room temperature. The mixture is then concentrated by evaporation to dryness and the residue is dissolved in 50 ml. of 1N hydrochloric acid. The acidic solution is washed with ethyl ether, then treated with aqueous sodium bicarbonate, and the precipitate is collected. The collected solid is then stirred with distilled water, refiltered and washed in this manner three more times, then dried overnight at 55° C affording a crude product which is then purified by recrystallization from benzene-cyclohexane affording 2.3 g. of 1-methyl-4,5-dihydro-5-(3-methoxyphenyl)-2-methoxycarbonylaminoimidazole, m.p. 137°–138° C.

By following the procedure set forth in part A of Example 1, the hydrochloride salt is prepared, m.p. 130°–133° C.

The nitrate salt (HNO₃) of 1-methyl-4,5-dihydro-5-(3-methoxyphenyl)-2-methoxycarbonylaminoimidazole, is prepared by dissolving 1-methyl-4,5-dihydro-2-methoxycarbonylamino-4-(3-methoxyphenyl)-imidazole in a few milliliters of ethanol and an equimolar amount of 70% aqueous nitric acid. The nitrate salt is then caused to crystallize by addition of ethyl ether until the solution turns just slightly turbid. Similarly, by following the same procedure, the nitrate salt of the following products is also respectively prepared.

B. Similarly, by following the same procedure of Part A but using the corresponding substituted phenyl or unsubstituted phenyl-β-amino-ethylamine starting materials in place of β-amino-β-(3-methoxyphenyl)-ethylamine. The following compounds are respectively prepared.

1-methyl-4,5-dihydro-5-(4-methoxyphenyl)-2-methoxycarbonylaminoimidazole;
1-methyl-4,5-dihydro-5-(2-methoxyphenyl)-2-methoxycarbonylaminoimidazole;
1-methyl-4,5-dihydro-5-(2-ethoxyphenyl)-2-methoxycarbonylaminoimidazole;
1-methyl-4,5-dihydro-5-(3-ethoxyphenyl)-2-methoxycarbonylaminoimidazole;
1-methyl-4,5-dihydro-5-(4-ethoxyphenyl)-2-methoxycarbonylaminoimidazole;
1-methyl-4,5-dihydro-5-(4-isopropoxyphenyl)-2-methoxycarbonylaminoimidazole
1-methyl-4,5-dihydro-5-(3-t-butoxyphenyl)-2-methoxycarbonylaminoimidazole;
1-methyl-4,5-dihydro-5-(3-pentoxyphenyl)-2-methoxycarbonylaminoimidazole;
1-methyl-4,5-dihydro-5-(4-hydroxyphenyl)-2-methoxycarbonylaminoimidazole;
1-methyl-4,5-dihydro-5-(3-hydroxyphenyl)-2-methoxycarbonylaminoimidazole; and
1-methyl-4,5-dihydro-5-(2-hydroxyphenyl)-2-methoxycarbonylaminoimidazole.

C. Similarly, by following the same procedure of parts A and B but respectively replacing the 1-mono and 1,3-bis(methoxycarbonyl)-S-methylisothiourea mixture with the corresponding 1-mono- and 1,3-bis(alkoxycarbonyl)-S-methylisothiourea mixtures, e.g. the corresponding 2-ethoxycarbonylamino, 2-isopropoxycarbonylamino, 2-butoxycarbonylamino-2-n-pentoxycarbonylamino, and 2-n-hexyloxycarbonylamino derivatives of each of the above representative compounds are respectively prepared.

D. Similarly, by following the same procedure of parts A and B but respectively replacing the β-methylamino-β-(3-methoxyphenyl)-ethylamine with other β-alkylamino-β-(alkoxyphenyl)-ethylamines such as β-isopropylamino-β-(alkoxyphenyl)-ethylamine, β-t-butylamino-β-(alkoxyphenyl)-ethylamine, β-isoamylamino-β-(alkoxyphenyl)-ethylamine, β-isohexylamino-β-(alkoxyphenyl)-ethylamine, or β-n-hexylamino-β-(alkoxyphenyl)-ethylamine, the corresponding 1-alkyl-4,5-dihydro-5-(alkoxyphenyl)-2-methoxycarbonylaminoimidazoles such as 1-ethyl-4,5-dihydro-5-(alkoxyphenyl)-2-methoxycarbonylaminoimidazole;

1-t-butyl-4,5-dihydro-5-(alkoxyphenyl)-2-methoxycarbonylaminoimidazole;

1-isoamyl-4,5-dihydro-5-(alkoxyphenyl)-2-methoxycarbonylaminoimidazole;
1-(2-t-butylethyl)-4,5-dihydro-5-(alkoxyphenyl)-2-methoxycarbonylaminoimidazole, and
1-n-hexyl-4,5-dihydro-5-(alkoxyphenyl)-2-methoxycarbonylaminoimidazole
are obtained. Similarly, by following the procedure of part C of this example, other corresponding 2-alkoxycarbonylaminoimidazoles represented above may be prepared.

EXAMPLE 3

A. This example illustrates methods, according to the invention, of preparing the halo substituted phenyl and trifluoromethyl substituted phenyl compounds of the invention. In this example, 4.0 g. of the dihydrochloride salt of β-methylamino-β-(2-fluorophenyl)-ethylamine is dissolved in 10 ml. of water, then filtered to remove any insoluble impurities and then diluted to a volume of 100 ml. by the addition of isopropanol. A few ml. of saturated sodium bicarbonate is then added and the resulting mixture stirred for five minutes. 4.5 Grams of a mixture of 1-mono and 1,3-bis (methoxycarbonyl)-S-methylisothiourea in 75 ml. of chloroform is then added and the resulting mixture is stirred for 4 days at room temperature, and then concentrated by evaporation to near dryness. The resulting residue is allowed to stand in 50 ml of 1N hydrochloric acid for 1 hour, then washed with ethyl either and benzene and filtered. The filtrate is then treated with saturated aqueous sodium bicarbonate, the resulting precipitate is collected, washed twice with water, and then dried in vacuum affording a crude product which is then recrystallized from isopropanol affording 2.95 g. of 1-methyl-4,5-dihydro-5-(2-fluorophenyl)-2-methoxycarbonylaminoimidazole, m.p. 178°–180° C.

The hydrochloride or nitrate salt of this compound or those listed below may be prepared by following the procedure of part A of Examples 1 or 2.

The hydrobromide salt of 1-methyl-4,5-dihydro-5-(3-fluorophenyl)-2-methoxycarbonylaminoimidazole, is prepared by treating 1-methyl-4,5-dihydro-5-(3-fluorophenyl)-2-methoxycarbonylaminoimidazole with about an equimolar amount of concentrated hydrobromic acid in acetone. Toluene is added and all solvents removed under reduced pressure affording a gummy residue, which is then refluxed under ethyl ether for six hours yielding a solidified hydrobromide salt product. Similarly, by following the same procedure, the corresponding hydrobromide salts of each of the compounds listed below are respectively prepared.

B. Similarly, by following the same procedure but using the corresponding β-methylamino-β-(substituted phenyl)-ethylamine starting material in place of β-methylamino-β-(3-fluorophenyl)-ethylamine, the following compounds are respectively prepared.

1-methyl-4,5-dihydro-5-(4-fluorohenyl)-2-methoxycarbonylaminoimidazole;
1-methyl-4,5-dihydro-5-(2-fluorophenyl)-2-methoxycarbonylaminoimidazole;
1-methyl-4,5-dihydro-5-(2-chlorophenyl)-2-methoxycarbonylaminoimidazole, m.p. 153°–155° C;
1-methyl-4,5-dihydro-5-(4-chlorophenyl)-2-methoxycarbonylaminoimidazole; m.p. 184°–186° C;
1-methyl-4,5-dihydro-5-(3-chlorophenyl)-2-methoxycarbonylaminoimidazole;

1-methyl-4,5-dihydro-5-(2-bromophenyl)-2-methoxycarbonylaminoimidazole;
1-methyl-4,5-dihydro-5-(4-bromophenyl)-2-methoxycarbonylaminoimidazole;
1-methyl-4,5-dihydro-5-(2-iodophenyl)-2-methoxycarbonylaminoimidazole;
1-methyl-4,5-dihydro-5-(3-iodophenyl)-2-methoxycarbonylaminoimidazole;
1-methyl-4,5-dihydro-5-(4-iodophenyl)-2-methoxycarbonylaminoimidazole;
1-methyl-4,5-dihydro-5-(4-trifluoromethylphenyl)-2-methoxycarbonylaminoimidazole; m.p. 229°–230° C;
1-methyl-4,5-dihydro-5-(2-trifluoromethylphenyl)-2-methoxycarbonylaminoimidazole; and
1-methyl-4,5-dihydro-5-(3-trifluoromethylphenyl)-2-methoxycarbonylaminoimidazole.

C. Similarly, by following the same procedure but respectively replacing the 1-mono and 1,3-bis(methoxycarbonyl)-S-methylisothiourea mixtures with the corresponding 1-mono- and 1,3-bis(alkoxycarbonyl)-S-methylisothiourea mixtures, the corresponding 2-ethoxycarbonylamino, 2-isopropoxycarbonylamino-2-isobutoxycarbonylamino, 2-n-butoxycarbonylamino, 2-isoamyloxycarbonylamino and 2-n-hexlyoxycarbonylamino derivatives of each of the above compounds are respectively prepared, for example
1-methyl-4,5-dihydro-5-(2-chlorophenyl)-2-ethoxycarbonylaminoimidazole; m.p. 117°–118° C; hydrochloride salt 167°–170° C.
1-methyl-4,5-dihydro-5-(3-chlorophenyl)-2-ethoxycarbonylaminoimidazole.

D. Similarly, by following the same procedure of parts A and B but respectively replacing the β-methylamino-β-(2-fluorophenyl)-ethylamine with other β-alkylamino-β-(substituted phenyl)-ethylamines such as β-ethylamino-β-(substituted phenyl)-ethylamine, β-n-propylamino-β-(substituted phenyl)-ethylamine, β-sec-butylamino-β-(substituted phenyl)-ethylamine, β-isopentylamino-β-(substituted phenyl)-ethylamine, β-t-pentylamino-β-(substituted phenyl)-ethylamine, or β-n-hexylamino-β-(substituted phenyl)-ethylamine, the corresponding 1-alkyl-4,5-dihydro-5-(substituted phenyl)-2-methoxycarbonylaminoimidazoles such as 1-ethyl-4,5-dihydro-5-(substituted phenyl)-2-methoxycarbonylaminoimidazole;
1-n-propyl-4,5-dihydro-5-(substituted phenyl)-2-methoxycarbonylaminoimidazole;
1-t-butyl-4,5-dihydro-5-(substituted phenyl)-2-methoxycarbonylaminoimidazole;
1-isopentyl-4,5-dihydro-5-(substituted phenyl)-2-methoxycarbonylaminoimidazole;
1-t-pentyl-4,5-dihydro-5-(substituted phenyl)-2-methoxycarbonylaminoimidazole;
1-n-hexyl-4,5-dihydro-5-(substituted phenyl)-2-methoxycarbonylaminoimidazole
are obtained. Similarly, by following the procedure of part C of this example, other corresponding 2-alkoxycarbonylaminoimidazoles of the "1-alkyl" compounds represented above may be prepared.

EXAMPLE 4

This example illustrates methods according to the invention of preparing the methylenedioxy substituted phenyl compounds of the invention. In this example 9.0 g. of the dihydrochloride salt of β-methylamino-β-(3,4-methylenedioxyphenyl)-ethylamine is dissolved in 40 ml. of water. This solution is stirred and added successively to it is 150 ml. of isopropanol, 4.1 g. of sodium methoxide and finally 8 g. of a mixture of 1-mono and 1,3-bis(methoxycarbonyl)-S-methylisothiourea in 100 ml. of chloroform. The mixture is then stirred for 12 days at room temperature. It is then concentrated under vacuum affording a gummy residue which is then incompletely dissolved in 100 ml. of approximately 1N aqueous hydrochloric acid. The resulting mixture is first filtered and then washed with ethyl ether, heated with charcoal and filtered again. The crude product is then precipitated from the filtrate by addition of aqueous sodium bicarbonate. The precipitate is collected by filtration, stirred with distilled water, collected again and then dried under vacuum affording crude of 1-methyl-4,5-dihydro-5-(3,4-methylenedioxyphenyl)-2-methoxycarbonylaminoimidazole which is recrystalized from isopropanol yielding the purified product. A hydrogen-ion addition salt may be prepared according to the methods set forth in part A of Examples 1–3.

B. The 1-methyl-4,5-dihydro-5-(2,3-methylenedioxyphenyl)-2-methoxycarbonylamino is similarly prepared.

C. Similarly, by following the same procedure of part A using the corresponding 1-mono and 1,3-bis(alkoxycarbonyl)-S-methylisothiourea starting material in place of 1,3-bis(methoxycarbonyl)-S-methylisothiourea, the following representative compounds are prepared:
1-methyl-4,5-dihydro-5-(3,4-methylenedioxyphenyl)-2-ethoxycarbonylaminoimidazole; and
1-methyl-4,5-dihydro-5-(3,4-methylenedioxyphenyl)-2-pentoxycarbonylaminoimidazole.

D. By following the same procedure of parts A and B but respectively replacing β-methylamino-β-(3,4-methylenedioxyphenyl)-ethylamine with other β-alkylamino-β-(3,4- (or 2,3-)methylenedioxyphenyl)-ethylamines such as β-ethylamino-β-(3,4-methylenedioxy)phenylethylamine, and the like, the corresponding "1-alkyl" compounds of this invention such as 1-ethyl-4,5-dihydro-5-(3,4-methylenedioxyphenyl)-2-methoxycarbonylaminoimidazole,
1-t-pentylamine-β-(2,3-methylenedioxyphenyl)-2-methoxycarbonylaminoimidazole, and the like
are obtained. Similarly by following the procedure of part C of this example, other corresponding 2-alkoxycarbonylaminoimidazoles of the "1-alkyl" compounds represented above may be prepared.

EXAMPLE 5

A. This example illustrates methods according to the invention of preparing the dialkyl substituted phenyl compounds of the invention. In this example, 50 ml. of isopropanol and 1.8 g. of sodium methoxide is added to a solution contraining 4.2 g. of the dihydrochloride salt of β-methylamino-β-(2,3-dimethylphenyl)-ethylamine dissolved in 10 ml. of water. The mixture is stirred for 15 minutes and then a solution containing 3.4 g. of a mixture of 1-mono and 1,3-bis(methoxycarbonyl)-S-methylisothiourea in 50 ml. of chloroform is added and then stirred for about two weeks at room temperature. The mixture is then concentrated by evaporation to near dryness and swirled with water, collected, and stirred in 50 ml. of aqueous 1 Normal hydrochloric acid for one hour. The resulting mixture is washed with ethyl ether, then treated with aqueous sodium bicarbonate and filtered. The collected solid is then stirred with distilled water, refiltered and washed in this manner three more times, then dried overnight at room temperature affording a crude product which is then puriified by recrystallization from isopropanol affording 1-methyl-4,5-dihydro-5-(2,3-dimethylphenyl)-2-methoxycarbonylaminoimidazole.

Hydrogen-ion addition salts of this compound as well as those in parts B-D below may be prepared according to the procedures of part A of Examples 1-4.

B. Similarly, by following the same procedure but using the corresponding disubstituted phenyl-β-methylamino-ethylamine, especially, the 2,3- or 2,5-disubstituted phenyl-β-methylaminoethylamine, starting materials in place of β-methylamino-β-(2,3-dimethylphenyl)-ethylamine, the following compounds are respectively prepared:

1-methyl-4,5-dihydro-5-(3,6-dimethylphenyl)-2-methoxycarbonylaminoimidazole;
1-methyl-4,5-dihydro-5-(2,5-dimethylphenyl)-2-methoxycarbonylaminoimidazole;
1-methyl-4,5-dihydro-5-(2,4-dimethylphenyl)-2-methoxycarbonylaminoimidazole;
1-methyl-4,5-dihydro-5-(2,5-diethylphenyl)-2-methoxycarbonylaminoimidazole;
1-methyl-4,5-dihydro-5-(2,3-diethylphenyl)-2-methoxycarbonylaminoimidazole;
1-methyl-4,5-dihydro-5-(2,5-di-t-butylphenyl)-2-methoxycarbonylaminoimidazole;
1-methyl-4,5-dihydro-5-(3,5-di-t-butylphenyl)-2-methoxycarbonylaminoimidazole;
1-methyl-4,5-dihydro-5-(2,5-di-n-hexylphenyl)-2-methoxycarbonylaminoimidazole;
1-methyl-4,5-dihydro-5-(2,4-di-n-hexylphenyl)-2-methoxycarbonylaminoimidazole; and
1-methyl-4,5-dihydro-5-(2,5-di-isopentylphenyl)-2-methoxycarbonylaminoimidazole.

C. Similarly, by following the same procedure of parts A and B but respectively replacing the 1-mono and 1,3-bis(methoxycarbonyl)-S-methylisothiourea mixture with the corresponding 1-mono- and 1,3-bis(alkoxycarbonyl)-S-methylisothiourea mixtures, e.g. corresponding 2-ethoxycarbonylamino, 2-isopropoxycarbonylamino, 2-isobutoxycarbonylamino, and 2-n-pentoxycarbonylamino derivatives of each of the above compounds are respectively prepared.

D. Similarly, by following the same procedure of parts A and B but respectively replacing the β-methylamino-β-(2,3-diphenyl)-ethylamine with other β-alkylamino-β-(dialkyphenyl)-ethylamino such as β-ethylamino-β-(dialkylphenyl)-ethylamine, β-isopropylamino-β-(dialkylphenyl)-ethylamine, β-t-butylamino-β(dialkylphenyl)-ethylamine, β-isoamylamino-β-(dialkylphenyl)-ethylamine, β-isohexylamino-β-(dialkylphenyl)-ethylamine, or β-n-hexylamino-β-(substituted phenyl)-ethylamine, the corresponding 1-alkyl-4,5-dihydro-5-(dialkylphenyl)-2-methoxycarbonylaminoimidazoles such as 1-ethyl-4,5-dihydro-5-(dialkylphenyl)-2-methoxycarbonylaminoimidazole;
1-isopropyl-4,5-dihydro-5-(dialkylphenyl)-2-methoxycarbonylaminoimidazole;
1-t-butyl-4,5-dihydro-5-(dialkylphenyl)-2-methoxycarbonylaminoimidazole;
1-isoamyl-4,5-dihydro-5-(dialkylphenyl)-2-methoxycarbonylaminoimidazole;
1-isohexyl-4,5-dihydro-5-(dialkylphenyl)-2-methoxycarbonylaminoimidazole;
1-n-hexyl-4,5-dihydro-5-(dialkylphenyl)-2-methoxycarbonylaminoimidazole.

Similarly, by following the procedure of part C of this example, other corresponding 2-alkoxycarbonylaminoimidazoles of the "1-alkyl" compounds represented above may be prepared.

EXAMPLE 6

A. This example illustrates methods according to the invention of preparing the compounds of the invention having dialkoxy or dihydroxy substituents on the phenyl ring. In this example, 50 ml. of isopropanol and 1.25 g. of sodium methoxide is added to a solution containing 3.15 g. of the dihydrochloride salt of β-methylamino-β-(3,5-dimethoxyphenyl)-ethylamine dissolved in 10 ml. of water. The mixture is stirred for 15 minutes and then a solution containing 2.6 g. of 1-mono and 1,3-bis(methoxycarbonyl)-S-methylisothiourea mixture in 40 ml. of chloroform is added and then stirred for about two weeks at room temperature. The mixture is then concentrated by evaporation to dryness and stirred in 100 ml. of aqueous 0.5 Normal hydrochloric acid for one hour. The resulting solution is washed with ethyl ether, then treated with aqueous sodium bicarbonate and filtered. The collected solid is then stirred with distilled water, refiltered, then dried ovenight at 55° C affording 1.68 g. of a crude product which is then purified by recrystallization from 200 ml. of benzene affording 1-methyl-4,5-dihydro-4-(3,5-dimethoxyphenyl)-2-methoxycarbonylaminoimidazole. The corresponding acid addition salts of this compound and others listed hereafter are prepared according to procedures in Examples 1-5, part A.

B. Similarly, by following the same procedure but using the corresponding dihydrophenyl or dialkoxyphenyl-β-methylaminoethylamine starting materials in place of β-methylamino-β-(3,5-dimethoxyphenyl)-ethylamine. The following compounds are respectively prepared.

1-methyl-4,5-dihydro-5-(2,3-dimethoxyphenyl)-2-methoxycarbonylaminoimidazole;
1-methyl-4,5-dihydro-5-(2,3-dimethoxyphenyl)-2-methoxycarbonylaminoimidazole;
1-methyl-4,5-dihydro-5-(2,5-dimethoxyphenyl)-2-methoxycarbonylaminoimidazole;
1-methyl-4,5-dihydro-5-(2,6-dimethoxyphenyl)-2-methoxycarbonylaminoamidazole;
1-methyl-4,5-dihydro-5-(3,4-dimethoxyphenyl)-2-methoxycarbonylaminoimidazole;
1-methyl-4,5-dihydro-5-(2,5-diisopropoxyphenyl)-2-methoxycarbonylaminoimidazole;
1-methyl-4,5-dihydro-5-(2,3-diisopropoxyphenyl)-2-methoxycarbonylaminoimidazole;
1-methyl-4,5-dihydro-5-(3,4-diisopropoxyphenyl)-2-methoxycarbonylaminoimidazole;
1-methyl-4,5-dihydro-5-(2,3-n-hexyloxyphenyl)-2-methoxycarbonylaminoimidazole;
1-methyl-4,5-dihydro-5-(2,5-n-hexyloxyphenyl)-2-methoxycarbonylaminoimidazole;
1-methyl-4,5-dihydro-5-(3,5-n-hexyloxyphenyl)-2-methoxycarbonylaminoimidazole;
1-methyl-4,5-dihydro-5-(2,3-dihydroxyphenyl)-2-methoxycarbonylaminoimidazole;

1-methyl-4,5-dihydro-5-(2,6-dihydroxyphenyl)-2-methoxycarbonylaminoimidazole;

1-methyl-4,5-dihydro-5-(2,5-dihydroxyphenyl)-2-methoxycarbonylaminoimidazole;

1-methyl-4,5-dihydro-5-(2,4-dihydroxyphenyl)-2-methoxycarbonylaminoimidazole; and 1-methyl-4,5-dihydro-5-(3,5-dihydroxyphenyl)-2-methoxycarbonylaminoimidazole.

C. Similarly, by following the same procedure but respectively replacing the 1-mono and 1,3-bis(methoxycarbonyl)-S-methylisothiourea mixture with the corresponding 1-mono- and 1,3-bis(alkoxycarbonyl)-S-methylisothiourea mixtures, e.g. the corresponding representative 2-ethoxycarbonylamino, 2-isopropoxycarbonylamino and 2-n-pentoxycarbonylamino derivatives of each of the above compounds are respectively prepared.

D. Similarly, by following the same procedure of parts A and B but respectively replacing the β-methylamino-β-(2,3-dimethoxyphenyl)-ethylamine with other β-alkylamino-β-(substituted phenyl)-ethylamino such as β-ethylamine-β-(substituted phenyl)-ethylamine, β-isopropylamino-β-(substituted phenyl)-ethylamine, β-t-butylamino-β-(substituted phenyl)-ethylamine, β-n-butylamino-β-(substituted phenyl)-ethylamine, or β-sec-hexylamino-β-(substituted phenyl)-ethylamine, the corresponding 1-alkyl-4,5-dihydro-5-(substituted phenyl)-2-methoxycarbonylaminoimidazoles are prepared. Similarly, by following the procedure of part C of this example, other corresponding 2-alkoxycarbonylaminoimidazoles of the "1-alkyl" compounds represented above may be prepared.

EXAMPLE 7

A. This example illustrates methods, according to the invention, of preparing the difluoro substituted phenyl and ditrifluoromethyl substituted phenyl compounds of the invention. In this example, g. of the dihydrochloride salt of β-methylamino-β-(3,4-difluorophenyl)-ethylamine is dissolved in 10 ml. of water, then filtered to remove any insoluble impurities and then diluted to a volume of 40 ml. by the addition of isopropanol. 0.9 Grams of sodium methoxide is then added and the resulting mixture stirred for five minutes. 3.4 Grams of a 1-mono and 1,3bis(methoxycarbonyl)-S-methylisothiourea mixture in 35 ml. of chloroform is then added and the resulting mixture is stirred for 12 days at room temperature, and then concentrated by evaporation to near dryness. The resulting residue is stirred with water and collected by filtration, dissolved in 30 ml. of 2% aqueous hydrochloric acid, then washed with ethyl ether and benzene and filtered. The collected solid is then treated with saturated aqueous sodium bicarbonate, filtered, washed twice with water, and then dried in vacuum affording a crude product which is then recrystallized from methanol affording 1-methyl-4,5-dihydro-5-(3,4-difluorophenyl)-2-methoxycarbonylaminoimidazole. Pharmaceutically acceptable hydrogen in addition salts are prepared according to the procedures of part A of Examples 1–6.

B. Similarly, by following the same procedure but using the corresponding β-(difluoro-substituted phenyl)-β-methylaminoethylamine or β-(ditrifluoromethyl substituted phenyl)-β-methylamino-ethylamine starting material in place of β-methylamino-β-(3,4-difluorophenyl)-ethylamine, the following compounds are respectively prepared:

1-methyl-4,5-dihydro-5-(2,3-difluorophenyl)-2-methoxycarbonylaminoimidazole;

1-methyl-4,5-dihydro-5-(2,5-difluorophenyl)-2-methoxycarbonylaminoimidazole;

1-methyl-4,5-dihydro-5-(2,6-difluorophenyl)-2-methoxycarbonylaminoimidazole;

1-methyl-4,5-dihydro-5-(2,4-difluorophenyl)-2-methoxycarbonylaminoimidazole;

1-methyl-4,5-dihydro-5-(3,5-difluorophenyl)-2-methoxycarbonylaminoimidazole;

1-methyl-4,5-dihydro-5-(2,3-ditrifluoromethylphenyl)-2-methoxycarbonylamino;

1-methyl-4,5-dihydro-5-(2,4-ditrifluoromethylphenyl)-2-methoxycarbonylaminoimidazole;

1-methyl-4,5-dihydro-5-(2,5-ditrifluoromethylphenyl)-2-methoxycarbonylamino;

1-methyl-4,5-dihydro-5-(2,6-ditrifluoromethylphenyl)-2-methoxycarbonylaminoimidazole;

1-methyl-4,5-dihydro-5-(3,4-ditrifluoromethylphenyl)-2-methoxycarbonylaminoimidazole; and 1-methyl-4,5-dihydro-5-(3,5-ditrifluoromethylphenyl)-2-methoxycarbonylaminoimidazole.

C. Similarly, by following the same procedure but respectively replacing the 1-mono- and 1,3-bis(methoxycarbonyl)-S-methylisothiourea mixture with, e.g., 1-mono and 1,3-bis(ethoxycarbonyl)-S-methylisothiourea, 1-mono and 1,3-bis(isobutoxycarbonyl)-S-methylisothiourea, and 1-mono-1,3-bis(n-pentoxycarbonyl)-S-methylisothiourea the corresponding 2-ethoxycarbonylamino(e.g. 1-methyl-4,5-dihydro-5-(3,4-difluorophenyl)-2-ethoxycarbonylaminoimidazole, 2-butoxycarbonylamino (e.g. 1-methyl-4,5-dihydro-5-(3,4-difluorophenyl)-2-isobutoxycarbonylaminoimidazole and 2-n-pentoxycarbonylamino derivatives of each of the above compounds are respectively prepared.

D. Similarly, by following the same procedure of part A but respectively replacing the β-methylamino-β-(3,4-difluorophenyl)-ethylamine with other β-alkylamino-β-(substituted phenyl)-ethylamines such as, e.g., β-isopropylamino-β-(difluorosubstituted phenyl)-ethylamine, β-t-butylamino-β-(di-trifluoromethyl substituted phenyl)-ethylamine, β-isopentylamino-β-(difluoro substituted phenyl)ethylamine, β-isohexylamino-β-(di-trifluoromethyl substituted phenyl)-ethylamine, or β-n-hexylamino-β-(difluoro substituted phenyl)-ethylamine, the corresponding 1-alkyl-4,5-dihydro-5-(difluoro substituted phenyl)-2-methoxycarbonylaminoimidazole or 1-alkyl-4,5-dihydro-5-(di-trifluoromethylphenyl)-2-methoxycarbonylaminoimidazoles, are prepared, i.e.

1-isopropyl-4,5-dihydro-5-(difluorophenyl)-2-methoxycarbonylaminoimidazole;

1-t-butyl-4,5-dihydro-5-(trifluoromethyl substituted phenyl)-2-methoxycarbonylaminoimidazole;

1-isopentyl-4,5-dihydro-5-(difluoro substituted phenyl)-2-methoxycarbonylaminoimidazole;

1-isohexylethyl)-4,5-dihydro-5-(ditrifluoromethyl substituted phenyl)-2-methoxycarbonylaminoimidazole;

1-n-hexyl-4,5-dihydro-5-(difluoro substituted phenyl)-2-methoxycarbonylaminoimidazole.

Similarly, by following the procedure of part C of this example, other corresponding 2-alkoxycarbonyl aminoimidazoles of the "1-alkyl" compounds represented above may be prepared.

EXAMPLE 8

A. This example illustrates methods, according to the invention, of preparing the dichloro, dibromo, and diiodo substituted phenyl compounds of the invention. In this example, 4.8 g. of the dihydrochloride salt of β-methylamino-β-(3,4-dichlorophenyl)ethylamine is dissolved in 20 ml. of water, then filtered to remove any insoluble impurities and then diluted to a volume of 100 ml. by the addition of isopropanol. 1.7 Grams of sodium methoxide is then added and the resulting mixture stirred for five minutes. 3.2 G. of a 1-mono and 1,3-bis(-methoxycarbonyl)-S-methylisothiourea in 80 ml. of chloroform is then added and the resulting mixture is stirred for 12 days at room temperature, and then concentrated by evaporation to near dryness. The resulting residue is stirred with water and collected by filtration, dissolved in 200 ml. of 2% aqueous hydrochloric acid, then washed with ethyl ether and benzene and filtered. The collected solid is then treated with saturated aqueous sodium bicarbonate, filtered, washed twice with water, and then dried in vacuum affording a crude product, which is then recrystallized from methanol affording 1-methyl-4,5-dihydro-5-(3,4-dichlorophenyl)-2-methoxycarbonylaminoimidazole. The hydrogen-ion addition salts of this compound may be prepared by methods discussed hereinbefore.

B. Similarly, by following the same procedure but using the corresponding β-(3,4-disubstituted phenyl)-β-methylaminoethylamine starting material in place of β-methylamino-β-(3,4-dichlorophenyl)-ethylamine, the following compounds are respectively prepared.

1-methyl-4,5-dihydro-5-(2,3-dichlorophenyl)-2-methoxycarbonylaminoimidazole;
1-methyl-4,5-dihydro-5-(2,5-dichlorophenyl)-2-methoxycarbonylaminoimidazole;
1-methyl-4,5-dihydro-5-(2,6-dichlorophenyl)-2-methoxycarbonylaminoimidazole;
1-methyl-4,5-dihydro-5-(2,4-dichlorophenyl)-2-methoxycarbonylaminoimidazole;
1-methyl-4,5-dihydro-5-(3,5-dichlorophenyl)-2-methoxycarbonylaminoimidazole;
1-methyl-4,5-dihydro-5-(3,4-dibromophenyl)-2-methoxycarbonylaminoimidazole;
1-methyl-4,5-dihydro-5-(2,6-dibromophenyl)-2-methoxycarbonylaminoimidazole;
1-methyl-4,5-dihydro-5-(3,5-dibromophenyl)-2-methoxycarbonylaminoimidazole;
1-methyl-4,5-dihydro-5-(2,5-diiodophenyl)-2-methoxycarbonylaminoimidazole;
1-methyl-4,5-dihydro-5-(2,3-diiodophenyl)-2-methoxycarbonylaminoimidazole; and
1-methyl-4,5-dihydro-5-(2,6-diiodophenyl)-2-methoxycarbonylaminoimidazole.

C. Similarly, by following the same procedure but respectively replacing the 1-mono- and 1,3-bis(methoxycarbonyl)-S-methylisothiourea mixture with, e.g., 1-mono and 1,3-bis(ethoxycarbonyl)-S-methylisothiourea; 1-mono and 1,3-bis(isobutoxycarbonyl)-S-methylisothiourea; and 1-mono-1,3-bis(n-pentoxycarbonyl)-S-methylisothiourea the corresponding 2-ethoxycarbonylamino, 2-isobutoxycarbonylamino and 2-n-pentoxycarbonylamino derivatives of each of the above compounds are respectively prepared.

D. Similarly, by following the same procedure of part A but respectively replacing the β-methylamino-β-(3,4-dichlorophenyl)-ethylamine with other alkylamino-(substituted phenyl)-ethylamino such as β-isopropylamino-β-(dichloro substituted Phenyl)-ethylamine, β-t-butylamino-β-(dibromo substituted phenyl)-ethylamine, β-isoamylamino-β-(diiodo substituted phenyl)-ethylamine, β-isohexylamino-β-(dichloro substituted phenyl)-ethylamine, or β-n-hexylamino-β-(dibromo substituted phenyl)-ethylamine, the corresponding 1-alkyl-4,5-dihydro-5-(substituted phenyl)-2-methoxycarbonylaminoimidazoles such as 1-isopropyl-4,5-dihydro-5-(dichloro substituted phenyl)-2-methoxycarbonylaminoimidazole;
1-t-butyl-4,5-dihydro-5-(dibromo substituted phenyl)-2-methoxycarbonylaminoimidazole;
1-isoamyl-4,5-dihydro-5-(diiodo substituted phenyl)-2-methoxycarbonylaminoimidazole;
1-isohexyl-4,5-dihydro-5-(dichloro substituted phenyl)-2-methoxycarbonylaminoimidazole;
1-n-hexyl-4,5-dihydro-5-(dibromo substituted phenyl)-2-methoxycarbonylaminoimidazole.

Similarly, by following the procedure of part C of this example, other corresponding 2-alkoxycarbonylaminoimidazoles of the "1-alkyl" compounds represented above may be prepared.

EXAMPLE 9

This example illustrates methods, according to the invention, of preparing the 2-alkoxycarbonylamino compounds of the invention where a mixture of the mono and the 1,3-bis(alkoxycarbonylamino)-S-methylisothiourea is prepared and used in situ. In this example a mixture of 2.8 g. of S-methyl-2-thiopseudourea sulfate, 4.3 g. of iso-butyl chloroformate and 15 ml. of water is stirred in an ice bath. To this mixture is added 6.0 ml. of 20%, by wt., of aqueous sodium hydroxide, in three portions and stirring is continued for two hours after which time the mixture is extracted with 30 ml. of chloroform. This chloroform extract is added to a stirred mixture of 3.3 g. of β-methylamino-β-phenylethylamine dihydrochloride and 12 ml. of saturated aqueous sodium bicarbonate in 50 ml. of isopropanol. After six days, the mixture is evaporated in vacuo to dryness and the residue is stirred with 100 ml. of 0.5N hydrochloric acid for 20 minutes. The resulting solution is washed with ethyl ether four times and twice with toluene. Saturated solution of aqueous sodium bicarbonate is added and the resulting precipitate is collected, stirred with distilled water, recollected and dried in vacuo at 55° C, affording 1-methyl-4,5-dihydro-5-phenyl-2-iso-butoxycarbonylaminoimidazole; m.p. 103°–104°. Recrystallization from cyclohexane did not change the m.p.

Similarly, by following the same procedure but using the corresponding β-alkylamino-β-phenyl (or substituted phenyl)-ethylamines as starting materials, the corresponding 2-iso-butoxycarbonylamino derivatives of each of the free base products, prepared in Examples 1–8, are respectively prepared.

Similarly, by following the same procedure but using the corresponding alkyl chloroformate and β-alkylamino-β-phenyl (or substituted phenyl)-ethylamine dihydrochloride starting materials, the corresponding 1-alkyl-4,5-dihydro-5-(substituted phenyl)-2-alkoxycarbonylaminoimidazoles are prepared.

EXAMPLE 10

This example illustrates another method, according to the invention, of preparing the 2-n-hexyloxycarbonylamino compounds of the invention. In this example, 5.25 g. of the dihydrochloride salt of β-methylamino-β-phenylethylamine is dissolved in 40 ml. of water, then filtered to remove any insoluble impurities and then diluted to a volume of 150 ml. by the addition of isopropanol. 2.4 Grams of sodium methoxide is then added and the resulting mixture stirred for five minutes. 4.5 Grams of a mixture of mono and 1,3-bis(n-hexyloxycarbonyl)-S-methylisothiourea in 75 ml. of chloroform is then added and the resulting mixture is stirred for 12 days at room temperature, and then concentrated by evaporation to near dryness. The resulting residue is stirred with water and collected by filtration, dissolved in 70 ml. of 2% aqueous hydrochloric acid, then washed with ethyl ether and benzene and filtered. The collected solid is then treated with saturated aqueous sodium bicarbonate, filtered, washed twice with water, and then dried in vacuum affording a crude 1-methyl-4,5-dihydro-5-phenyl-2-n-hexyloxycarbonylaminoimidazole product, which is then further purified by recrystallization from methanol.

Similarly, by following the same procedure but using β-alkylamino-β-phenyl-ethylamine and the corresponding β-alkylamino-β-(substituted phenyl)-ethylamine as starting materials, the corresponding 2-n-hexyloxycarbonylamino derivatives of each of the free base products, prepared in Examples 1-8, are respectively prepared.

EXAMPLE 11

This example illustrates another process embodiment of the invention for preparing compounds of the invention from the corresponding 1-alkyl-4,5-dihydro-5-(phenyl or substituted phenyl)-2-aminoimidazole. In this example, 35 g. of 1-methyl-2-amino-4-phenyl-2-imidazoline hydrobromide is stirred in a solution of one molar equivalent (7.4 g.) of sodium methoxide in excess isopropyl alcohol. After about 20 minutes, the mixture is filtered and the filtrate is concentrated under reduced pressure. The residue is refluxed for 2½ hours with 300 ml. of dimethyl carbonate during which time a total of 60 ml. of the refluxing solvent is removed by means of a Dean-Starck trap. The mixture is cooled to room temperature and the solid collected and recrystallized from 800 ml. of methanol, affording 1-methyl-4,5-dihydro-5-phenyl-2-methoxycarbonylaminoimidazole.

Similarly, by following the same procedure but using the corresponding 1-alkyl 2-amino-5-substituted phenyl-2-imidazoline hydrobromide and the corresponding dialkylcarbonates as starting materials, the free base products of Examples 1-10, are respectively prepared.

The hydrochloride salt of 1-methyl-4,5-dihydro-5-phenyl-2-methoxycarbonylaminoimidazole, is prepared by dissolving the corresponding free base (i.e. 1-methyl-4,5-dihydro-5-phenyl-2-methoxycarbonylaminoimidazole) in 0.5N hydrochloric acid and then removing most of the water under reduced pressure. Residual amounts of water are removed by addition of isopropanol and toluene and subsequent removal of the solvents under reduced pressure. The resulting solid hydrochloride salt can be recrystallized from isopropanol. Similarly, by following the same procedure, the hydrochloride salt of each of the above products is also respectively prepared.

EXAMPLE 12

This example illustrates the preparation of the pure (+) optical isomers of the invention. In this example, starting with (+) β-methylamino-β-phenylethylamine and following the procedure of Example 1, there is obtained (+) 1-methyl-4,5-dihydro-5-phenyl-2-methoxycarbonylaminoimidazole.

Similarly, the corresponding (+) isomers of the products prepared in Examples 1-11 are respectively prepared by repeating the procedures of Examples 1-11 but using the respective pure (+) optical isomers of β-alkylamino-β-phenyl (or substituted phenyl)-ethylamine as starting materials in Examples 1-10 and the respective pure (+) optical isomers of 1-alkyl-2-amino-4,5-dihydro-5-(phenyl or substituted phenyl)imidazole as starting materials in Example 11, in place of the racemic starting materials,

EXAMPLE 13

This example illustrates methods according to the invention of preparing mono- and dihydroxy substituted phenyl compounds of the invention. In this example, 3.0 g. of β-methylamino-β-(3,4-dibenzyloxyphenyl)ethylamine is dissolved in 50 ml of ethanol and 2 ml of water. The solution is combined with a solution of 1.7 g of a mixture of 1-mono and 1,3-bis (methoxycarbonyl)-S-methylisothiourea in 25 ml of chloroform and allowed to stand for 8 days and then concentrated to dryness. The residue is treated with 100 ml of 0.5N hydrochloric acid and the resulting slurry is stirred vigorously in the presence of ethyl ether. Stirring is discontinued and the ether layer is removed by decantation. This process is repeated four times and the remaining aqueous slurry is then treated in the excess of saturated aqueous sodium bicarbonate solution. The product, 1-methyl-4,5-dihydro-5-(3,4-dibenzyloxyphenyl)-2-methoxycarbonylaminoimidazoline, is extracted into chloroform, the chloroform is removed and the remaining product is purified by recrystallization from 300 ml of benzene. By treating the resulting free base with a solution of 10 ml of ethanol that contains 400 mg of hydrogen chloride and then with 200 ml of ether, the hydrochloride salt is obtained. A sample of the hydrochloride salt of 1-methyl-4,5-dihydro-5-(3,4-dibenzyloxyphenyl)-2-methoxycarbonylaminoimidazole is treated according to a standard hydrogenolysis procedure using palladium-on-charcoal catalyst in ethanol and hydrogen gas at atmospheric pressure, to afford the hydrochloride salt of 1-methyl-4,5-dihydro-5-(3,4-dihydroxyphenyl)-methoxycarbonylaminoimidazole.

Similarly, by following the same procedure but using the appropriate β-alkylamino-β-([di]benzyloxyphenyl)ethylamine and 1-mono and 1,3-bis(alkoxycarbonyl)-S-methylisothiourea, other mono- or dihydroxyphenyl compounds may be prepared such as 1-methyl-4,5-dihydro-5-(2-hydroxyphenyl)-2-methoxycarbonylaminoimidazole;
1-ethyl-4,5-dihydro-5-(3-hydroxyphenyl)-2-methoxycarbonylaminoimidazole;
1-isopropyl-4,5-dihydro-5-(4-hydroxyphenyl)-2-methoxycarbonylaminoimidazole;
1-n-pentyl-4,5-dihydro-5-(2,6-dihydroxyphenyl)-2-methoxycarbonylaminoimidazole;
1-methyl-4,5-dihydro-5-(2,5-dihydroxyphenyl)-2-ethoxycarbonylaminoimidazole;

1-methyl-4,5-dihydro-5-(2,4-dihydroxyphenyl)-2-isopropoxycarbonylaminoimidazole;

1-methyl-4,5-dihydro-5-(2,3-dihydroxyphenyl)-2-t-butoxycarbonylaminoimidazole; and 1-methyl-4,5-dihydro-5-(3,5-dihydroxyphenyl)-2-methoxycarbonylaminoimidazole.

EXAMPLE 14

This example illustrates the preparation of the pure (−) optical isomers of the invention. In this example, starting with (−) β-methylamino-β-phenylethylamine and following the procedure of Example 1, there is obtained (−) 1-methyl-4,5-dihydro-5-phenyl-2-methoxycarbonylaminoimidazole.

Similarly, the corresponding (−) isomers of the products prepared in Examples 1–11 are respectively prepared by repeating the procedures of Examples 1–11 but using the respective pure (−) optical isomers of β-alkylamino-β-phenyl (or substituted phenyl)-ethylamine as starting materials in Examples 1–10 and the respective pure (−) optical isomers of 1-alkyl-2-amino-4,5-dihydro-5-(phenyl or substituted phenyl)imidazole as starting materials in Example 11, in place of the racemic starting materials.

EXAMPLE 15

This example illustrates methods for preparing the pharmaceutically acceptable salts of the invention.

In this example, 500 mg. of 1-methyl-4,5-dihydro-5-phenyl-2methoxycarbonylaminoimidazole and 280 mg. of maleic acid are refluxed together in 50 ml. of methylenechloride until only traces of insoluble materials are left. The solution is filtered and the filtrate is treated with ethyl ether. The resulting precipitated maleate salt is collected by filtration and dried under vacuum, affording the maleate salt of 1-methyl-4,5-dihydro-5-phenyl-2-methoxycarbonylaminoimidazole.

Similarly, by following the same procedure, but respectively using the free base products of Examples 1–13, the corresponding maleate salts of these products are respectively prepared.

EXAMPLE 16

This example illustrates another process embodiment of the invention wherein an alkyl chloroformate is used as one of the reagents. In the example, 0.8 g. of methyl chloroformate is added over a five minute period to a stirring mixture of 2 g. 1-methyl-2-amino-5-phenyl-2-imidazoline hydrobromide, 1.4 g. sodium bicarbonate, and 20 ml. acetone held at 0° C. After addition is complete, the mixture is allowed to warm to room temperature and then stirred for 16 hours at room temperature. The mixture is distilled to a low volume and 50 ml. of water is then added. The mixture is filtered and the precipitate collected and washed with water and then dried affording 1-methyl-4,5-dihydro-5-phenyl-2-methoxycarbonylaminoimidazole which is then further purified by recrystallization from chloroform.

Similarly, by following the same procedure but using the corresponding 1-alkyl-2-amino-5-(substituted phenyl)-2-imidazoline hydrobromides and the corresponding alkyl chloroformates as starting materials, the free base products of Examples 1–10, are respectively prepared.

EXAMPLE 17

This example illustrates the process of the invention wherein 1-(mono)-alkoxycarbonyl-S-methylisothiourea is used in place of a mixture of the mono- and bis-alkoxycarbonyl-reagents. In this example, a solution containing 2.1 g. of β-methylamino-β-phenylethylamine dihydrochloride, 1.64 g. of sodium acetate and 2.4 g. of 1-methoxycarbonyl-S-methylisothiourea in 20 ml. of 50%, wt., aqueous methanol is gently refluxed for two hours. The resulting heavy slurry is cooled, filtered and the collected solid product then washed with methanol affording 1-methyl-4,5-dihydro-5-phenyl-2-methoxycarbonylaminoimidazole.

Similarly, the free base products of Examples 1–9 are respectively prepared by following the procedures of these examples but replacing the 1-mono- and 1,3-bis-alkoxycarbonyl-S-methylisothiourea mixtures, used in Examples 1–9, with the corresponding 1-alkoxycarbonyl-S-methylisothiourea.

Obviously many modifications and variations of the invention, described hereinabove and below in the claims, can be made without departing from the scope and essence thereof.

EXAMPLE 18

This example illustrates a process of the invention for preparing 1-methyl-4,5-dihydro-5-phenyl-2-alkoxycarbonylaminoimidazoles.

A solution of 0.45 g β-methylamino-β-phenylethylamine dihydrochloride in 3 ml water is treated with 0.34 g sodium bicarbonate. The mixture is stirred briefly and a solution of 0.42 g 1,3-bismethoxycarbonyl-2-methylthiourea in 6 ml methanol is added. The mixture is heated to reflux for about 2 hours whereupon 3 ml. methanol are distilled out. The mixture is cooled and the precipitate is filtered off. The white crystalline precipitate is washed with methanol and water and is dried, yielding 1-methyl-4,5-dihydro-5-phenyl-2-methoxycarbonylaminoimidazole. Similarly by following the above procedure but substituting other 1,3-bisalkoxycarbonyl-2-methylureas for 1,3-bismethoxycarbonyl-2-methylurea, other compounds of this invention are prepared.

EXAMPLE 19

A mixture of 16 g calcium cyanamide, 15 ml ethanol and 60 ml water is stirred for 1½ hours, then 10.7 ml methylchloroformate are added over 20 minutes, while controlling the temperature of the mixture between 30° and 40° C. The mixture is stirred for 1 hour and filtered. The filter cake is washed with 20 ml water. The filtrate is adjusted to pH7 and 8 g β-methylamino-β-phenylethylamine dihydrochloride are added. The solution is heated to 70° C for 16 hours. The solution is cooled and the white precipitate is collected by filtration. The cake is washed with water and the crude 1-methyl-4,5-dihydro-5-phenyl-2-methoxycarbonylaminoimidazole dried. The material is recrystallized from methanol/chloroform.

EXAMPLE 20

This example illustrates a process for preparing the free base of a compound represented by formula I from the corresponding acid salt by reacting the salt with an organic or inorganic base under conditions suitable to convert the salt to the free base. In this example the hydrochloride salt of 1-methyl-4,5-dihydro-5-(2-methylphenyl)-2-methoxycarbonylaminoimidazole is dissolved in water at room temperature. A slight molar excess of saturated sodium bicarbonate is added until the reaction is complete. The free base is extracted with ethyl acetate and the solvent is removed by evaporation. Other compounds of this invention prepared as set forth in examples 1-19 as salts may be similarly converted to the corresponding free base using appropriate solvents and bases. Suitable bases include inorganic bases such as alkali metal carbonates or bicarbonates, alkali metal lower alkoxides, alkali metal hydroxides alkaline earth hydroxides, and mixtures thereof as well as organic bases such as pyridine, triethylamine, diazabicyclononane, and the like.

We claim as our invention:

1. A compound selected from those represented by the formula

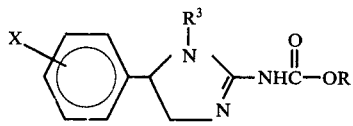

wherein
R and $R^3$ are each independently lower alkyl and the total number of carbon atoms in R and $R^3$ together is an integer of two through seven and
X is hydrogen, fluoro, chloro, bromo, iodo, alkyl of one through six carbon atoms, hydroxy, alkoxy of one through six carbon atoms, or trifluoromethyl and the pharmaceutically acceptable salts thereof.

2. The compound of claim 1 wherein X is hydrogen, hydroxy, methoxy, ethoxy, n-propoxy, isopropoxy, fluoro, chloro, bromo, iodo, alkyl of one through three carbon atoms, or trifluoromethyl and the total number of carbon atoms in R and $R^3$ together is 2 or 3.

3. The compound of claim 2 wherein both R and $R^3$ are methyl.

4. The compound of claim 3 wherein the compound is chosen from the group of 1-methyl-4,5-dihydro-5-phenyl-2-methoxycarbonylaminoimidazole and the pharmaceutically acceptable salts thereof.

5. The compound of claim 2 chosen from the group of 1-methyl-4,5-dihydro-5-(2-methylphenyl)-2-methoxycarbonylaminoimidazole and the pharmaceutically acceptable salts thereof.

6. The compound of claim 2 chosen from the group of 1-methyl-4,5-dihydro-5-(3-methylphenyl)-2-methoxycarbonylaminoimidazole and the pharmaceutically acceptable salts thereof.

7. The compound of claim 2 chosen from the group of 1-methyl-4,5-dihydro-5-(3-methoxyphenyl)-2-methoxycarbonylaminoimidazole and the pharmaceutically acceptable salts thereof.

8. The compound of claim 2 chosen from the group of 1-methyl-4,5-dihydro-5-phenyl-2-ethoxycarbonylaminoimidazole and the pharmaceutically acceptable salts thereof.

9. The compound of claim 2 chosen from the group of 1-methyl-4,5-dihydro-5-(2-chlorophenyl)-2-ethoxycarbonylaminoimidazole and the pharmaceutically acceptable salts thereof.

10. The compound of claim 2 chosen from the group of 1-methyl-4,5-dihydro-5-(2-fluorophenyl)-2-ethoxycarbonylaminoimidazole and the pharmaceutically acceptable salts thereof.

11. The compound of claim 2 chosen from the group of 1-ethyl-4,5-dihydro-5-phenyl-2-methoxycarbonylaminoimidazole and the pharmaceutically acceptable salts thereof.

12. The compound of claim 2 chosen from the group consisting of 1-methyl-4,5-dihydro-5-(3-bromophenyl)-2-methoxycarbonylaminoimidazole and the pharmaceutically acceptable salts thereof.

13. The compound of claim 2 chosen from the group consisting of 1-methyl-4,5-dihydro-5-(3-trifluoromethylphenyl)-2-methoxycarbonylaminoimidazole and the pharmaceutically acceptable salts thereof.

14. The compound of claim 1 wherein X is hydrogen, hydroxy, fluoro or chloro.

15. The compound of claim 14 chosen from the group of 1-methyl-4,5-dihydro-5-(2-fluorophenyl)-2-methoxycarbonylaminoimidazole and the pharmaceutically acceptable salts thereof.

16. The compound of claim 14 chosen from the group of 1-methyl-4,5-dihydro-5-(3-fluorophenyl)-2-methoxycarbomnylaminoimidazole and the pharmaceutically acceptable salts thereof.

17. The compound of claim 14 chosen from the group of 1-methyl-4,5-dihydro-5-(4-fluorophenyl)-2-methoxycarbonylaminoimidazole and the pharmaceutically acceptable salts thereof.

18. The compound of claim 14 chosen from the group of 1-methyl-4,5-dihydro-5-(2-chlorophenyl)-2-methoxycarbonylaminoimidazole and the pharmaceutically acceptable salts thereof.

19. The compound of claim 14 chosen from the group of 1-methyl-4,5-dihydro-5-(4-chlorophenyl)-2-methoxycarbonylaminoimidazole and the pharmaceutically acceptable salts thereof.

20. The compound of claim 14 chosen from the group consisting of 1-methyl-4,5-dihydro-5-(2-fluorophenyl)-2-isopropoxycarbonylaminoimidazole and the pharmaceutically acceptable salts thereof.

21. The compound of claim 14 chosen from the group consisting of 1-methyl-4,5-dihydro-5-(2-chlorophenyl)-2-isopropoxycarbonylaminoimidazole and the pharmaceutically acceptable salts thereof.

22. The compound of claim 14 chosen from the group consisting of 1-methyl-4,5-dihydro-5-(3-chlorophenyl)-2-methoxycarbonylaminoimidazole and the pharmaceutically acceptable salts thereof.

23. The compound of claim 14 chosen from the group consisting of 1-methyl-4,5-dihydro-5-(3-chlorophenyl)-2-ethoxycarbonylaminoimidazole and the pharmaceutically acceptable salts thereof.

24. The compound of claim 1 wherein the total number of carbon atoms in R and $R^3$ taken together is 4 and

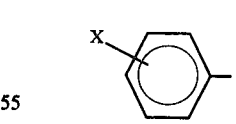

is 2-bromophenyl; 4-bromophenyl; 2-iodophenyl; 2-methylphenyl; 3-methylphenyl; 2-methoxyphenyl; or 4-methoxyphenyl.

25. The compound of claim 1 wherein the total number of carbon atoms in R and $R^3$ taken together is 5 and

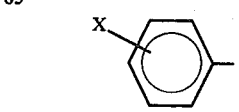

is 2-bromophenyl; 3-ethylphenyl; 2-methoxyphenyl; 4-methoxyphenyl; 2-iodophenyl; 4-ethylphenyl; and 4-ethoxyphenyl.

26. The compound of claim 1 chosen from the group of 1-methyl-4,5-dihydro-5-phenyl-2-isobutoxycarbonylaminoimidazole and the pharmaceutically acceptable salts thereof.

27. A pharmaceutical composition useful for palliating or inhibiting psychic disorders, centrally induced musculoskeletal disorders or convulsive disorders in a mammal which comprises an effective amount of the compound of claim 1 and a pharmaceutically acceptable carrier.

28. A method of tranquilizing or sedating a mammal which comprises administering to said mammal an effective amount of about 0.01 to 300 mg/kg of compound of claim 1.

29. A method of palliating conditions of depression, etiopathic to the central nervous system, in mammals, which comprises administering to said mammals an effective amount of about 0.01 to about 50 mg/kg of the compound of claim 1 which is chosen from the group consisting of (A) a compound wherein the total number of carbons in R and $R^3$ together is 2 or 3 and X is hydrogen, fluoro, chloro, bromo, iodo, alkyl of 1–3 carbons, trifluoromethyl, hydroxy, or alkoxy of 1–3 carbon atoms;

(B) a compound wherein the total number of carbon atoms in R and $R^3$ taken together is an integer of 2 through 7 and X is hydrogen, fluoro, chloro or hydroxy;

(C) A compound wherein R and $R^3$ are both methyl and X is alkyl of four through seven carbon atoms;

(D) a compound wherein the total number of carbon atoms in R and $R^3$ is 4 and X is methyl, trifluoromethyl, 2-bromo, 4-bromo, 2-methoxy, 4-methoxy or 2-iodo;

(E) a compound wherein the total number of carbon atoms in R and $R^3$ together is 5 and X is 2-bromo, 3-ethyl, 2-methoxy, 4-methoxy, 4-ethyl, or 4-ethoxy;

(F) a compound wherein the total number of carbon atoms in R and $R^3$ together is 6 and X is 2-methoxy; and (G) the pharmaceutically acceptable salts of compounds (A)–(F).

30. The method of claim 29 wherein said compound is chosen from the group consisting of 1-methyl-4,5-dihydro-5-(2-chloro-phenyl)-2-isopropoxycarbonylaminoimidazole and the pharmaceutically acceptable salts thereof.

31. The method of claim 29 wherein said compound is chosen from the group consisting of 1-methyl-4,5-dihydro-5-(2-fluorophenyl)-2-isopropoxycarbonylaminoimidazole and the pharmaceutically acceptable salts thereof.

32. The method of claim 29 wherein said compound is chosen from the group consisting of 1-methyl-4,5-dihydro-5-(3-chlorophenyl)-2-methoxycarbonylaminoimidazole and the pharmaceutically acceptable salts thereof.

33. The method of claim 29 wherein said compound is chosen from the group consisting of 1-methyl-4,5-dihydro-5-(3-bromophenyl)-2-methoxycarbonylamimoimidazole and the pharmaceutically acceptable salts thereof.

34. The method of claim 29 wherein said compound is chosen from the group consisting of 1-methyl-4,5-dihydro-5-(3-trifluoromethylphenyl)-2-methoxycarbonylaminoimidazole and the pharmaceutically acceptable salts thereof.

35. The method of claim 29 wherein said compound is chosen from the group consisting of 1-methyl-4,5-dihydro-5-(3-chlorophenyl)-2-ethoxycarbonylaminoimidazole and the pharmaceutically acceptable salts thereof.

36. A pharmaceutical composition useful for palliating conditions of depression, etiopathic to the central nervous system which comprises a pharmaceutical carrier and an effective amount of a compound of claim 1 chosen from the group consisting of (A) a compound wherein the total number of carbons in R and $R^3$ together is 2 or 3 and X is hydrogen, fluoro, chloro, bromo, iodo, alkyl or 1–3 carbons, trifluoromethyl, hydroxy, or alkoxy of 1–3 carbon atoms;

(B) a compound wherein the total number of carbon atoms in R and $R^3$ taken together is an integer of 2 through 7 and X is hydrogen, fluoro, chloro or hydroxy;

(C) a compound wherein R and $R^3$ are both methyl and X is alkyl of four through seven carbon atoms;

(D) a compound wherein the total number of carbon atoms in R and $R^3$ is 4 and X is methyl, trifluoromethyl, 2-bromo, 4-bromo, 2-methoxy, 4-methoxy or 2-iodo (E) a compound wherein the total number of carbon atoms in R and $R^3$ together is 5 and X is 2-bromo, 3-ethyl, 2-methoxy, 4-methoxy, 4-ethyl, or 4-ethoxy;

(F) a compound wherein the total number of carbon atoms in R and $R^3$ together is 6 and X is 2-methoxy; and (G) the pharmaceutically acceptable salts of compounds of (A)–(F).

37. The pharmaceutical composition of claim 36 wherein said compound is chosen from the group consisting of 1-methyl-4,5-dihydro-5-(2-chlorophenyl)-2-isopropoxyaminoimidazole and the pharmaceutically acceptable salts thereof.

38. The pharmaceutical composition of claim 36 wherein said compound is chosen from the group consisting of 1-methyl-4,5-dihydro-5-(2-fluorophenyl)-2-isopropoxycarbonylaminoimidazole and the pharmaceutically acceptable salts thereof.

39. The pharmaceutical composition of claim 36 wherein said compound is chosen from the group consisting of 1-methyl-4,5-dihydro-5-(3-chlorophenyl)-2-methoxycarbonylaminoimidazole and the pharmaceutically acceptable salts thereof.

40. The pharmaceutical composition of claim 36 wherein said compound is chosen from the group consisting of 1-methyl-4,5-dihydro-5-(3-bromophenyl)- 2-methoxycarbonylaminimidazole and the pharmaceutically acceptable salts thereof.

41. The pharmaceutical composition of claim 36 wherein said compound is chosen from the group consisting of 1-methyl-4,5-dihydro-5-(3-trifluoromethylphenyl)-2-methoxycarbonylaminoimidazole and the pharmaceutically acceptable salts thereof.

42. The pharmaceutical composition of claim 36 wherein said compound is chosen from the group consisting of 1-methyl-4,5-dihydro-5-(3-chlorophenyl)-2- ethoxycarbonylaminoimidazole and the pharmaceutically acceptable salt thereof.

43. A compound selected from those represented by the formula

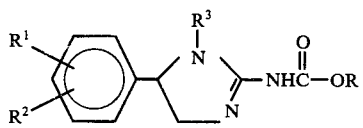

wherein
R and $R^3$ are each independently lower alkyl and the total number of carbon atoms in R and $R^3$ together is an integer of two through seven;
$R^1$ is at the 2-position on the phenyl ring and is chosen from the group of fluoro, chloro, bromo, iodo, hydroxy, alkoxy of one through six carbon atoms, alkyl of one through six carbon atoms, and trifluoromethyl; and
$R^2$ is the same as $R^1$ but is at the 3- or 5- position on the phenyl ring.

44. The compound of claim 43 wherein the total number of carbon atoms in R and $R^3$ together is 2 or 3.

45. A pharmaceutical composition useful for palliating or inhibiting psychic disorders, centrally induced musculoskeletal disorders or convulsive disorders in a mammal which comprises an effective amount of the compound of claim 43 and a pharmaceutically acceptable carrier.

46. A method of tranquilizing or sedating a mammal which comprises administering to said mammal an effective amount of about 0.01 to 300 mg/kg of compound of claim 43.

47. A compound selected from those represented by the formula

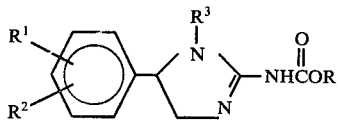

wherein
R and $R^3$ are each independently lower alkyl and the total number of carbon atoms in R and $R^3$ together is an integer of two through seven;
$R^1$ is fluoro, chloro, bromo, iodo, hydroxy, methoxy, ethoxy, or methyl at any position on the phenyl ring;
$R^2$ is the same as $R^1$ and is at any other position on the phenyl ring; and
$R^1$ and $R^2$ taken together may be methylenedioxy at adjacent positions on the phenyl ring.

48. The compound of claim 47 wherein $R^1$ and $R^2$ are each fluoro, chloro or hydroxy.

49. The compound of claim 48 wherein $R^1$ and $R^2$ are both fluoro.

50. The compound of claim 49 chosen from the group of 1-methyl-4,5-dihydro-5-(2,6-difluorophenyl)-2-methoxycarbonylaminoimidazole and the pharmaceutically acceptable salts thereof.

51. The compound of claim 48 chosen from the group of 1-methyl-4,5-dihydro-5-(2,6-dichlorophenyl)-2-methoxycarbonylaminoimidazole and the pharmaceutically acceptable salts thereof.

52. The compound of claim 47 wherein $R^1$ is at the ortho position, $R^1$ and $R^2$ are both chloro or are both bromo and the total number of carbon atoms in R and $R^3$ together is 2 through 5.

53. The compound of claim 47 wherein $R^1$ and $R^2$ are each iodo at an ortho position on the phenyl ring and the total number of carbon atoms in R and $R^3$ together is an integer of two through five.

54. The compound of claim 47 wherein $R^1$ and $R^2$ are each methyl and the total number of carbons in R and $R^3$ is 2 or 3.

55. A pharmaceutical composition useful for palliating or inhibiting psychic disorders, centrally induced musculoskeletal disorders or convulsive disorders in a mammal which comprises an effective amount of the compound of claim 47 and a pharmaceutically acceptable carrier.

56. A pharmaceutical composition useful for palliating conditions of depression, etiopathic to the central nervous system which comprises a pharmaceutical carrier and an effective amount of a compound of claim 47 chosen from the group consisting of
(A) a compound wherein the total number of carbon atoms in R and $R^3$ together is 2 through 4 and both $R^1$ and $R^2$ are bromo, with at least one bromo at the ortho position;
(B) a compound wherein the total number of carbon atoms in R and $R^3$ together is 2 through 7 and $R^1$ and $R^2$ together are dichloro, difluoro, or dihydroxy;
(C) a compound wherein the total number of carbons in R and $R^3$ together is 2 or 3 and $R^1$ and $R^2$ are both methyl;
(D) a compound wherein the total number of carbons in R and $R^3$ is 2, 3 or 4 and both $R^1$ and $R^2$ are ethoxy with at least one ethoxy being at the ortho position;
(E) a compound wherein the total number of carbon atoms in R and $R^3$ together is 2 through 6 inclusive and $R^1$ and $R^2$ are both methoxy;
(F) a compound wherein the total number of carbon atoms in R and $R^3$ together is 5 and $R^1$ and $R^2$ are 2,6-dibromo, 2,5-dimethyl, 2,5-dibromo, 2,3-dibromo, 2,5-dimethyl, or 3,5-dimethyl;
(G) a compound wherein the total number of carbon atoms in R and $R^3$ together is 7 and $R^1$ and $R^2$ are 2,6-dimethoxy;
(H) a compound wherein the total number of carbon atoms in R and $R^3$ together is 2 through 5 and $R^1$ and $R^2$ are 2,6-diiodo; and
(I) the pharmaceutically acceptable salts of compounds (A)-(H).

57. A method of palliating conditions of depression, etiopathic to the central nervous system, in mammals, which comprises administering to said mammals an effective amount of about 0.01 to about 50 mg/kg of a compound represented by the formula

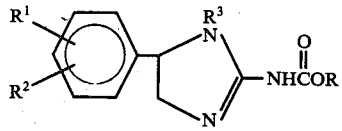

wherein said compound is chosen from the group consisting of
(A) a compound wherein the total number of carbon atoms in R and $R^3$ together is 2 through 4 and both $R^1$ and $R^2$ are bromo, with at least one bromo at the ortho position;

(B) a compound wherein the total number of carbon atoms in R and $R^3$ together is 2 through 7 and $R^1$ and $R^2$ together and dichloro, difluoro, or dihydroxy;

(C) a compound wherein the total number of carbons in R and $R^3$ together is 2 or 3 and $R^1$ and $R^2$ are both methyl;

(D) a compound wherein the total number of carbons in R and $R^3$ is 2, 3 or 4 and both $R^1$ and $R^2$ are ethoxy with at least one ethoxy being at the ortho position;

(E) a compound wherein the total number of carbon atoms in R and $R^3$ together is 2 through 6 inclusive and $R^1$ and $R^2$ are both methoxy;

(F) a compound wherein the total number of carbon atoms in R and $R^3$ together is 5 and $R^1$ and $R^2$ are 2,6-dibromo, 2,5-dimethyl, 2,5-dibromo, 2,3-dibromo, 2,5-dimethyl, or 3,5-dimethyl;

(G) a compound wherein the total number of carbon atoms in R and $R^3$ together is 7 and $R^1$ and $R^2$ are 2,6-dimethoxy;

(H) a compound wherein the total number of carbon atoms in R and $R^3$ together is 2 through 5 and $R^1$ and $R^2$ are 2,6-diiodo; and (I) the pharmaceutically acceptable salts of compounds (A)–(H).

* * * * *